(12) United States Patent
Chambon et al.

(10) Patent No.: US 6,203,795 B1
(45) Date of Patent: Mar. 20, 2001

(54) PHARMACEUTICAL COMPOSITION FOR THE TREATMENT OR PREVENTION OF A MALIGNANT TUMOR

(75) Inventors: Pierre Chambon, Blaesheim; Marie-Paule Kieny, Strasbourg, both of (FR); Richard Lathe, Leeds (GB); Mara Hareuveni, Ramai-Ha-Sharon (IL)

(73) Assignee: Transgene S.A., Strasbourg Cedex (FR)

( * ) Notice: Subject to any disclaimer, the term of this patent is extended or adjusted under 35 U.S.C. 154(b) by 0 days.

(21) Appl. No.: 09/083,116

(22) Filed: May 22, 1998

Related U.S. Application Data

(62) Division of application No. 08/479,537, filed on Jun. 7, 1995, now Pat. No. 5,861,381, which is a continuation of application No. 08/403,576, filed on Mar. 14, 1995, now abandoned, which is a continuation of application No. 08/039,320, filed as application No. PCT/FR91/00835 on Oct. 23, 1991, now abandoned.

(30) Foreign Application Priority Data

Oct. 23, 1990 (FR) .................................................. 90 13101

(51) Int. Cl.[7] ........................ A61K 39/00; C07K 14/435
(52) U.S. Cl. .................................... 424/185.1; 424/277.1; 530/350
(58) Field of Search ............................. 424/185.1, 277.1; 514/2; 530/350

(56) References Cited

FOREIGN PATENT DOCUMENTS

| | | | |
|---|---|---|---|
| 0 174 534 | * | 7/1988 | (EP) . |
| 0 369 816 | * | 5/1990 | (EP) . |
| 88-05054 | * | 7/1988 | (WO) . |
| 89-03492 | * | 4/1989 | (WO) . |
| 90-05142 | * | 5/1990 | (WO) . |

OTHER PUBLICATIONS

Keydar et al. (1989) Production and characterization of monoclonal antibodies identifying breast tumor–associated antigens. Proc. Natl. Acad. Sci. USA 86:1362–1366, Feb. 1989.*

Hareuveni et al. (1990) A transcribed gene, containing a variable number of tandem repeats, codes for a human epithelial tumor antigen. Eur. J. Biochem. 189:475–486, May 1990.*

Barnd et al. (1989) Proc. Natl. Acad. Sci. USA 86:7159–7163, 1989.*

Hareuveni et al. (1990) Proc. Natl. Acad. Sci. USA 87:9498–9502, 1990.*

Gendler et al. (1990) J. Biol. Chem. 265:15286–15293, 1990.*

Lightenberg et al. (1990) J. Biol. Chem. 265:5573–5578, 1990.*

Wreschner et al. (1990) Eur. J. Biochem. 189:463–473, 1990.*

* cited by examiner

Primary Examiner—Robert A. Schwartzman
(74) Attorney, Agent, or Firm—Burns, Doane, Swecker & Mathis, L.L.P.

(57) ABSTRACT

The application provides a polypeptide and a pharmaceutical composition which comprises said polypeptide, wherein said polypeptide is recognized by a particular antibody H23, which recognizes a particular tumor antigen expressed on breast cancer cells. This antibody specifically binds to an epitope comprising a tandem repeat sequence of 20 amino acids comprised in a transmembrane form as well as a secreted form of the polypeptides specifically bound by antibody H23.

40 Claims, 1 Drawing Sheet

PHARMACEUTICAL COMPOSITION FOR THE TREATMENT OR PREVENTION OF A MALIGNANT TUMOR

Figure 1:
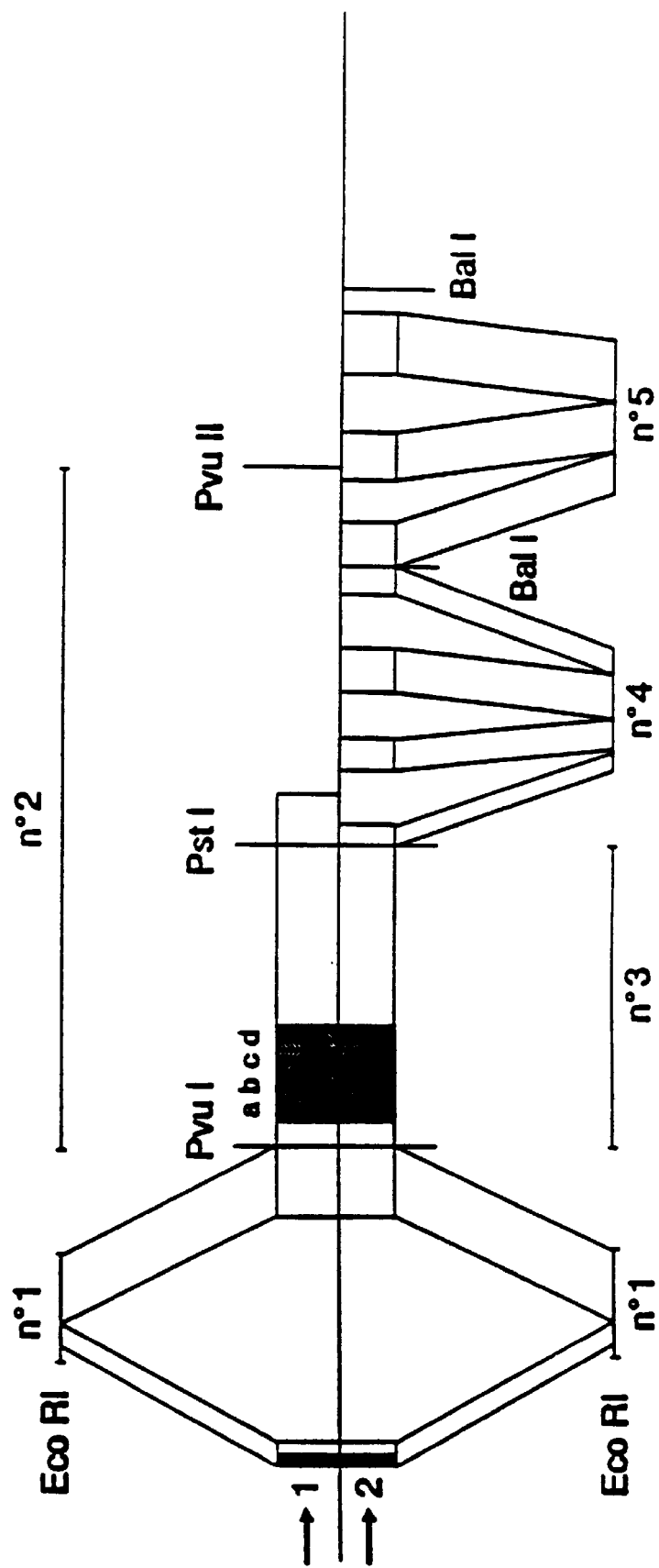

This application is a divisional of Application Ser. No. 08/479,537, filed Jun. 7, 1995, now U.S. Pat. No. 5,861,381, in turn a file wrapper continuation of Ser. No. 08/403,576, filed Mar. 14, 1995, now abandoned, in turn a file wrapper continuation of Application Ser. No. 08/039,320, filed Apr. 4, 1993, now abandoned, in turn a 371 of PCT/FR91/00835, filed Oct. 23, 1991.

The present invention relates to a pharmaceutical composition intended for the curative treatment or the prevention of a malignant tumor, more especially of a carcinoma and most especially of a breast cancer.

Most tumor cells express antigens at their surface which differ either qualitatively or quantitatively from the antigens present at the surface of the corresponding normal cells. These antigens are specific when they are expressed only by tumor cells. When they are present on both normal and tumor cells, these antigens are said to be associated with the tumor; in this case, they are present either in larger amounts or in a different form in the tumor cells.

The large majority of tumor antigens which have been characterized to date in man are human antigens associated with a tumor (hereinafter referred to as associated antigens). Among these, the following may be highlighted:

oncofetal antigens, such as carcinoembryonic antigen, which are present in fetal tissues and absent or in the trace state in the corresponding adult tissues; their expression is induced again in an aberrant manner during the development of a tumor;

differentiation antigens, which are normally expressed only during certain stages of maturation of a particular cell type; tumor cells which express such an antigen are considered to have their origin in a cell blocked in its differentiation;

the products of oncogenes which are beginning to be identified.

The specificity of an antigen associated with a tumor is hence quantitative rather than qualitative, since it may be present in a normal individual in a localized manner or intermittently (feto-embryonic period) or in the trace state, and becomes hyperexpressed (expression increased by a factor of 10 to 1000 times) only during a process of tumorigenesis. When this antigen is expressed normally, it is recognized by the immune system as part of the "Self", while its hyperexpression or its aberrant expression can trigger a humoral or cellular immune response.

Generally speaking, there are two major types of immune response: the humoral type response which is characterized by the production of antibodies by B lymphocytes, and the cell-mediated immune response which involves effector cells, i.e. essentially macrophages and cytotoxic T lymphocytes, as well as cells that regulate the immune response, i.e. helper and suppressor T lymphocytes.

A cell-mediated immune response necessitates the cooperation of helper T lymphocytes and effector cells. This cooperation takes place, in particular, as a result of interleukin-2 and various other lymphokines which are secreted by activated helper T lymphocytes. Interleukin-2 thereafter induces the action of cytotoxic T lymphocytes, and the lymphokines trigger the phagocytosis response of the macrophages. Concomitantly, there likewise exists a mechanism that suppresses the cell-mediated immune response which employs suppressor T lymphocytes.

It is now well known that patients suffering from a cancer may develop a humoral and cell-mediated immune response. This has been revealed, in particular, by demonstrating that the serum of some patients contained anti-tumor antigen antibodies, and that their serum was capable of inhibiting the growth of cancer cells in vitro. Nevertheless, inasmuch as spontaneous tumor regressions are extremely rare, it appears that the immune response observed in vitro remains ineffective in vivo. Similarly, it is also known that tumor grafts are not often rejected, even in immune animals, whereas allografts always are.

Although an immune response may develop against a tumor, it is doubtful whether it is of real benefit to the patient. Everything seems to indicate that a tumor eludes the body's mechanisms of immune surveillance. Various models have been proposed, to explain this phenomenon; for a complete and detailed review, see Scientific American, Medecine, Chapter 6, VIII Tumor Immunology, 1990. In principle, tumor antigens are considered to play a not insignificant part in modifying or diverting the immune response in favor of the tumor rather than in favor of the individual.

In the light of the complexity of the immune response against tumors and the mediocre state of current knowledge in this field, the use of an anticancer vaccine is not at all obvious. Animal studies have shown that immunization using living or killed cancer cells could lead to rejection of a subsequent tumor graft. Attempts at immunization using acellular products have generally been less successful.

To date, the possibility of manufacturing a vaccine against a cancer employing an antigen associated with this cancer hence remains controversial. A major theoretical objection to this method of treatment lies in the fact that an immune response is not considered to be sufficient to prevent or treat a tumor and that it is highly doubtful that a vaccine could be protective, that is to say capable of preventing or retarding the development of a tumor.

Nevertheless, it has now been found that a tumor antigen associated, inter alia, with breast cancer can, in vaccinal or therapeutic form, induce an immune response which protects against a subsequent tumor attack or one in the process of development. The antigen in question is, more specifically, the one recognized by the monoclonal antibody H23 derived from hybridoma ATCC No. HB 8630, deposited for the purposes of Patent Application EPA 174,534 and available to the public for experimental research work. Antibody H23 is, moreover, commercially available from Teva Pharmaceutical Industries Ltd, 5 Basel Street, Petah Tiqva, P.O. Box 1424, Tel-Aviv, Israel.

Antibody H23 was generated against particulate material present in the supernatant of in vitro cultures of the mammary tumor cell line T47D. Subsequently, it was shown that antibody H23 reacted markedly with a large majority of mammary tumor biopsies, as well as with the serum and other physiological fluids of patients with a breast cancer. In contrast, antibody H23 does not detect an antigen, or detect antigen only in the trace state, in the case of healthy individuals.

The tumor antigen recognized by antibody H23 is hence expressed in an aberrant manner by the epithelial cells of the cancerous mammary tissue in approximately 90% of cases of breast cancer whereas, in a normal individual, its expression is very low if not zero. Its presence in significant amounts has also been detected in tumoral epithelial tissues other than mammary epithelial tissues.

In a given patient, the tumor antigen recognized by antibody H23 exists in two forms: a transmembrane form and a secreted form, the amino acid sequences of which are shown, respectively, in the sequence identifiers (SI) Nos. 2 and 5 (SEQ ID NOS: 2 and 5). The transmembrane form and the secreted form both exhibit a high degree of polymorphism. In effect, the sequence of both forms of antigen comprises one particular subunit of 20 amino acids which is shown boxed in each SI and which may be repeated in tandem several times. The sequence of this subunit is of the formula (I) (SEQ ID NO: 3): Pro—Gly—Ser—Thr—Ala—Pro—X—Ala—His—Gly—Val—Thr—Ser—Ala—Pro—Asp—Y—Arg—Pro—X in which X is Pro or Ala and Y is Thr or Asn. From one individual to another, the number of tandem repeats can vary from 20 to 80 approximately and can, inter alia, characterize the polymorphic type. Lastly, it can happen that, from one repeat to another, a minimum number of amino acids (most often 1, 2 or 3 amino acids) is modified.

Moreover, it was established that the subunit of 20 amino acids described above was specific to the tumor antigen reacting with antibody H23, since this subunit contains the epitope recognized by this antibody.

Consequently, the invention provides a pharmaceutical composition intended for the curative treatment or the prevention of a malignant tumor, which comprises, as therapeutic agent, (i) a polypeptide recognized by antibody H23 or, alternatively, (ii) a virus into the genome of which a DNA fragment coding for a polypeptide recognized by antibody H23 is inserted, in combination with a diluent or vehicle which is acceptable from a pharmaceutical standpoint.

From a more general standpoint, the subject of the invention is also, as therapeutic agent for the treatment or prevention of a malignant tumor, a polypeptide recognized by antibody H23.

Similarly, the subject of the invention is also:

the use (i) of a polypeptide recognized by antibody H23, or, alternatively, the use (ii) of a virus into the genome of which a DNA fragment coding for a polypeptide recognized by antibody H23 is inserted, for treating or preventing a malignant tumor;

a method of curative treatment or prevention of a malignant tumor, which comprises the act of administering a therapeutically effective amount (i) of a polypeptide recognized by antibody H23 or, alternatively, (ii) of a virus into the genome of which a DNA fragment coding for a polypeptide recognized by antibody H23 is inserted, to a subject needing such a treatment. ("Therapeutically effective amount" is understood to mean an amount sufficient for implementing an effective therapy.)

A poypeptide recognized by antibody H23 can be, in particular, a polypeptide which comprises the sequence (I) (SEQ ID NO: 3): Pro—Gly—Ser—Thr—Ala—Pro—X—Ala—His—Gly—Val—Thr—Ser—Ala—Pro—Asp—Y—Arg—Pro—X in which X is Pro or Ala and Y is Thr or Asn. The sequence (I) (SEQ ID NO: 3) can be the complete sequence of the polypeptide recognized by antibody H23, or else can represent a single or repeated fragment of the polypeptide recognized by antibody H23.

A preferred polypeptide recognized by antibody H23 is a polypeptide recognized by antibody H23 whose sequence exhibits a degree of homology of at least 80%, preferably of at least 90% and, as a very special preference, from 95 to 100% inclusive with the sequence of the antigen of human epithelial tissue recognized by antibody H23 (in the text hereinafter, this antigen will be designated H23-ETA) in its transmembrane or secreted form.

As shown in SI No. 1 and 2 (SEQ ID NOS: 1 and 2) the transmembrane form of H23-ETA has an amino acid sequence beginning with the threonine residue at position 1 and ending with the leucine residue at position 414+(20×n) whereas, as shown in SI Nos. 4 and 5 (SEQ ID NOS: 4 and 5) the secreted form of H23-ETA has an amino acid sequence beginning with the threonine residue at position 1 and ending with the proline residue at position 246+(20×n). Quite generally speaking, n is a number from 1 to 80; preferably, n is a number from 1 to 40; as a very special preference, n is 2, 3 or 4.

More specifically, the transmembrane and secreted forms of H23-ETA have in common an N-terminal region of 106 amino acids (hereinafter referred to as the N-terminal region) and a middle region corresponding to the set of repeated subunits; in contrast, their C-terminal ends differ substantially. The amino acids from position 107+(20×n) to position 149+(20×n) are identical for both forms and vary from position 150+(20×n).

A preferred polypeptide recognized by antibody H23 whose sequence is not identical to one of those described in SI Nos. 2 and 5 (SEQ ID NOS: 2 and 5) is characterized by at least one mutation of an amino acid (point mutation) distributed at random in the N- or C-terminal regions. The number of total mutations must, of course, satisfy the criterion of degree of homology as established above. "Point mutation" is understood to mean the deletion or substitution of an amino acid of the N- or C-terminal region described in SI No. 1 or 2, as well as the addition of an amino acid within the N- or C-terminal region described in SI Nos. 2 and 5 (SEQ ID NOS: 2 and 5).

Generally speaking, a polypeptide recognized by antibody H23 may be produced by conventional methods of chemical synthesis or else, when the amino acid sequence comprises a large number of residues, by recombinant DNA techniques. More especially, a preparation method comprises the act of culturing a host microorganism transformed with a DNA fragment coding for a polypeptide recognized by antibody H23, and the act of harvesting said polypeptide from the culture. The host organism can be any microorganism capable of being transformed, for example and without limitation, a bacterium, a yeast or alternatively a mammalian cell, insofar as the DNA fragment in question is either integrated in the genome of the host organism or inserted into a suitable expression vector, that is to say capable of replicating in the host organism. Naturally, the DNA fragment coding for the polypeptide recognized by antibody H23 is placed under the control of regions containing suitable transcription and translation signals. Expression vectors and control regions are known to a person skilled in the art.

During the last decade, the use has been proposed of recombinant viruses as agents intended for inducing an immune response against miscellaneous pathogenic organisms. To this end, adenoviruses or pox viruses are most especially suitable. For use in the present invention, avian pox viruses, canarypox virus, or vaccinia virus are highly suitable. Vaccinia virus exhibits an immune cross-reaction with smallpox virus and, as a result, has been used as an anti-smallpox vaccinal agent since the 19th century. At the beginning of the 1980s, smallpox was considered to be eradicated from the earth's surface, and the World Health Organization consequently judged it preferable to stop vaccinating against smallpox. Hence vaccinia virus is now available for use in vaccines comprising a vaccinia virus whose genome has been modified so as to express heterologous genes coding for antigenic determinants specific to a vector organism of a disease other than smallpox.

Thus, the therapeutic agent of a pharmaceutical composition according to the invention can be, alternatively, a virus into the genome of which a DNA fragment coding for a polypeptide recognized by antibody H23 has been inserted.

This type of pharmaceutical composition has the advantage of being inexpensive to produce and of great stability under miscellaneous environmental conditions. In particular, the storage conditions impose no restrictions.

The general conditions for obtaining a vaccinia virus capable of expressing a block for expression of a heterologous protein are described in European Patent EP 83,286, the content of which is incorporated herein by reference. These conditions are applicable to other viruses which are acceptable as vectors, insofar as the latter possess at least one nonessential genomic region into which an expression block may be inserted.

A vaccinia virus into the genome of which a DNA fragment coding for a polypeptide recognized by antibody H23 is inserted may also be used as a particular expression vector for the purpose of producing said polypeptide in culture of mammalian cells, as stated above.

A polypeptide recognized by antibody H23, or a virus into the genome of which a DNA fragment coding for said polypeptide is inserted, exhibits in vivo antitumor activity in the following test: C3H line mice or Fisher line rats, aged 4 to 5 weeks, are treated twice, with an interval of ten days between the two treatments, with either between 10 and 500 µg of a polypeptide recognized by antibody H23, or between $10^7$ and $10^8$ pfu (plaque forming units) of a virus into the genome of which a DNA fragment coding for said polypeptide is inserted. When a polypeptide is used, the treatment is preferably performed by subcutaneous injection. A scarification of the tail is preferable in the case of a virus. Fifteen days after the first treatment, approximately $10^4$ to $10^7$ syngeneic tumor cells expressing H23-ETA, which have been cultured in vitro, treated with trypsin, washed and resuspended in PBS (phosphate buffered saline) buffer, are injected subcutaneously in a volume of approximately 100 µl. In parallel, untreated animals are likewise subjected to an identical tumor attack. Approximately 20 days after injection of the cells, the size of the subcutaneous tumors is smaller in the animals treated with a polypeptide or a virus than in untreated animals.

A polypeptide recognized by antibody H23, or a virus into the genome of which a DNA fragment coding for said polypeptide is inserted, is, as a result, useful for the purpose of treating or preventing a cancerous condition, more especially a carcinoma type tumor (tumor developed by epithelial cells), for example a mammary tumor.

For these indications, the appropriate dosage varies in accordance, for example, with the polypeptide or virus employed, the individual being treated, the mode of administration, the use as a vaccine or as a treatment. and the nature and severity of the tumor condition which is being treated. However, in general, the indications are that satisfactory vaccination results in mammals, for example humans, may be obtained with a virus, into the genome of which a DNA fragment coding for said polypeptide is inserted, at a single dosage, or dosage repeated once or twice at intervals of approximately 1 to 3 weeks, of approximately $10^4$ pfu/kg to approximately $10^8$ pfu/kg of body weight of the mammal.

A pharmaceutical composition according to the invention may be administered by any conventional route, especially the subcutaneous route, for example in the form of an injectable solution or suspension. As a vaccine, a composition according to the invention may be administered according to the modes conventionally implemented for already known vaccines, for example in a single dose or dose repeated one or several times after a certain lapse of time. When a composition according to the invention is being used in the curative treatment of a cancer, it may be administered frequently for a sufficient period for the treatment to be effective. Such a composition may advantageously be injected intratumorally.

A pharmaceutical composition according to the invention may be prepared according to conventional techniques. When the therapeutic agent is a vaccinia virus, this virus is preferably in attenuated live form. Attenuated viral strains are available at the present time; for example, the thymidine kinase-negative Copenhagen strain. To obtain the recombinant viruses needed for using a composition according to the invention, it suffices to use such a strain. Lastly, a recombinant virus may be attenuated by a suitable chemical treatment known to a person skilled in the art.

The invention is illustrated below, reference being made to FIG. 1.

FIG. 1 shows diagrammatically a genomic DNA fragment coding for the secreted form of H23-ETA (→1) or for the transmembrane form of H23-ETA (→2). The blocks and the gaps symbolize the exons and the introns, respectively. The black background corresponds to the signal sequence and the shaded background denotes the repeat sequences (of which there are 4: a, b, c and d). The DNA fragments Nos. 1 and 2 are used for the construction of a complete fragment coding for the secreted form of H23-ETA, whereas the fragments Nos. 3 to 5 are used for constructing a complete fragment coding for the transmembrane form of H23-ETA. The restriction sites shown in this figure are also to be found in SI Nos. 1 and 4 (SEQ ID NOS: 1 and 4).

EXAMPLE 1

Complementary and genomic DNA fragments coding for portions of a polypeptide that specifically binds H23 are isolated according to the procedure described in Wreschner et al., Eur. J. Biochem, (1990) 189: 463. These fragments are thereafter used to reconstruct a DNA fragment coding for the complete H23-ETA antigen in its secreted or transmembrane form.

The plasmid constructions are described below, reference being made to FIG. 1.

A. Preparation of a vaccinia virus capable of promoting the synthesis of the secreted form of H23-ETA.

An EcoRI-PvuII complementary DNA fragment (No. 1) is introduced between the EcoRI and PvuII sites of the multiple insertion region of the vector pPolyII described in Lathe et al., Gene (1987) 57: 193 to give plasmid pETA-5'. A PvuII genomic DNA fragment (No. 2), containing 4 repeat units, is introduced into the PvuII site of the multiple insertion region of pETA-5', downstream of the fragment No. 1 and in the appropriate orientation. In the repeat units a, b, c and d, the codons $xxx_1$ and $xxx_2$ are, respectively, CCA (Pro) and CCC (Pro), CCA and CCC, GCA (Ala) and GCC, CCA and GCC. Likewise, the codon yyy is ACC (Thr) in the repeat units a, b and c; the codon yyy is AAC (Asn) in the unit d.

A BamHI-SalI fragment coding for the complete secreted form of H23-ETA is excised from the plasmid finally obtained. This fragment is then inserted between the BamHI and SalI sites of the transfer vector ptg194-poly described in Kieny et al., Bio/Technology, (1986) 4:790, downstream of the vaccinia virus promoter E7.5k and inside the vaccinia virus gene coding for thymidine kinase.

The transfer vector obtained in the above paragraph is thereafter used to transfer the block for expression of the secreted form of H23-ETA into the genome of vaccinia virus, Copenhagen strain, according to the method described in Kieny et al., Nature (1984) 312: 163. The vaccinia virus VV-ETA-S is thereby obtained.

B. Preparation of a vaccinia virus capable of promoting the synthesis of the trans-membrane form of H23-ETA.

A PvuII-PstI genomic DNA fragment (No. 3), containing 4 repeat units, is introduced between the PvuII and PstI sites of the multiple insertion region of pETA-5', downstream of the fragment No. 1 and in the appropriate orientation. In the repeat units a, b, c and d, the codons $xxx_1$ and $xxx_2$ are, respectively, CCA (Pro) and CCC (Pro), CCA and CCC, GCA (Ala) and GCC, CCA and GCC. Likewise, the codon yyy is ACC (Thr) in the repeat units a, b and c; the codon yyy is AAC (Asn) in the unit d.

An EcoRI-PstI fragment corresponding to the cloned fragments is excised from the final plasmid obtained. The EcoRI cohesive end is converted to a blunt end by treatment with Klenow polymerase. This fragment is then introduced between the XhoI site, treated beforehand with Klenow polymerase, and the PstI site of the multiple insertion region of the vector pPolyII-Sfi/Not-14 described in Lathe et al., supra, to give plasmid pETA-T-5'.

A PstI-BalI complementary DNA fragment (No. 4) is introduced between the PstI and BalI sites of pETA-T-5'. A BalI-BalI complementary DNA fragment (No. 5) is then inserted into the BalI site of the plasmid finally obtained.

A BglII-SStI fragment coding for the complete transmembrane form of H23-ETA is excised from the plasmid obtained in the above paragraph; it is then introduced between the BanHI and SatI sites of the transfer vector ptgl86-poly described in Kieny et al., (1986), supra, downstream of the vaccinia virus promoter E7.5k and inside the vaccinia virus gene coding for thymidine kinase.

The transfer vector obtained in the above paragraph is thereafter used to transfer the block for expression of the transmembrane form of H23-ETA into the genome of vaccinia virus, Copenhagen strain (VV-O), according to the method described in Kieny et al., (1984), supra. The vaccinia virus VV-ETA-T is thereby obtained.

EXAMPLE 2: Preparation of virus stocks

Stocks of purified viruses are prepared using BHK-21 cells. BHK-21 cells are infected with the recombinant viruses VV-ETA-S and W-ETA-T (0.1 pfu/cell) for 48 hours. After this time, the cultures are frozen at −20° C. and then thawed at room temperature. After destruction of the cell walls by 3 successive treatments with a "Potter" in a hypotonic buffer, the soluble proteins of the supernatant are loaded onto a cushion of 36% (w/v) sucrose and centrifuged (Beckman SW 28, 1 h, 14 K). The pellet containing the virus is taken up in solution in 10 mM Tris—HCl pH 8 and placed on a linear (20–40%) sucrose gradient. After centrifugation (SW 28, 40 min, 14 K), the opalescent band containing the virus is withdrawn using a syringe and concentrated by centrifugation (SW 28, 20 K, 1 h). The virus is lastly taken up in a small volume of 10 mM Tris—Hcl pH 8 so as to obtain a viral stock assaying at approximately $10^{10}$ pfu/ml.

EXAMPLE 3: Tumor cell lines expressing H23-ETA

A. Construction of eukaryotic plasmids capable of promoting the expression of H23-ETA.

A BamHI-SalI DNA fragment coding for the secreted form of H23-ETA is excised from the plasmid obtained in Example 1A, first paragraph. It is then reintroduced between the BamHI and SalI sites of the multiple insertion region of plasmid pHMG described in Gautier et al., Nucl. Acid Res., (1989) I7 (20): 83, so as to be placed under the control of the promoter of the 3-hydroxy-3-methylglutarylcoenzyme A reductase (HMGCR) gene, downstream of the signal sequence of SV40 polyA. Plasmid pHMG-ETA-S is thereby obtained.

Likewise, plasmid pHMG-ETA-T is constructed in a similar manner by insertion of a BamHI-EcoRV DNA fragment derived from the plasmid obtained in Example 1B, paragraph 2.

B. Preparation of cell lines.

Cells of the tumor cell line FR3T3-ras-1, obtained from Fisher rat fibroblasts by Matriceau et al., EMBO J. (1985) 4: 1435, and cells of the mouse mammary carcinoma line MM5t, derived from C3H mice, are cotransfected (i) with pHMG-ETA-S and plasmid pAG60 described in Colbere-Garapin et al., J. Mol. Biol. (1981) 150: 1 which contains a gene for resistance to Geneticin (G418) or (ii) with pHMG-ETA-T and pAG60. To accomplish the transfection, the calcium phosphate precipitation method of Graham et al., Virology (1973) 52: 456 modified by Wigler et al., Cell (1978) 14: 725 is used.

The transfected clones are selected in the presence of 500 μl/ml of G418 and are thereafter cultured. Selection of the clones expressing H23-ETA is accomplished by labelling the cells with peroxidase after reaction with antibody H23. Cell lines in the pure state are obtained by the limiting dilution method, and the expression of H23-ETA is monitored.

The cell lines are designated as follows:

FR3T3-ras-1 (pAG60/pHMG-ETA-S): F-S

FR3T3-ras-1 (pAG60/pHNG-ETA-T): F-T

FR3T3-ras-1 (pAG60/pHMG): F-C

MM5tC3H (pAG60/pHMG-ETA-S): M-S

MM5tC3H (pAG60/pHMG-ETA-S): M-T

MM5tC3H (pAG60/pHMG-ETA-S): M-C

EXAMPLE 4: Demonstration of the vaccinal effect of H23-ETA

Fisher IOPS line male and female rats and C3H line female mice aged 4 to 5 weeks are immunized in the following manner: a purified viral preparation of VV-ETA-S, VV-ETA-T or VV-O is administered to the animals, by scarification of the tail, in a volume of 10 μl corresponding to approximately $2 \times 10^7$ pfu. This treatment is repeated 10 days later.

The F-S, F-T, F-C, M-S, M-T and M-C tumor lines are cultured in modified Dulbecco medium (Gibco) supplemented with 10% of fetal calf serum, 100 units of penicillin and 100 μg/ml of streptomycin. The cultures are then treated with trypsin, washed and suspended in PBS (phosphate buffered saline) buffer.

14 days after the first stage of immunization, $2 \times 10^4$ F-C cells, $4 \times 10^4$ F-S cells, $1.5 \times 10^5$ F-T cells or $2 \times 10^6$ M-C, M-S or M-T cells are injected subcutaneously into an animal in a volume of 100 μl.

The appearance of the subcutaneous tumors is monitored daily. The diameter of the tumors is measured in two dimensions. The complete data for the experiment and the results are presented in Table I below:

TABLE I

| Animal | Virus | Tumor cells | Number of animals having a tumor nodule relative to the total number of animals treated | Measured average diameter of the tumor nodules (in mm) x days after injection of the cells | | Percentage of animals free from tumors |
|---|---|---|---|---|---|---|
| Fisher line male rats | | F-C | 4/4 | 31 | (20 days) | 0 |
| | | F-S | 3/4 | 25 | (25 days) | 25 |
| | | F-T | 3/6 | 25 | (30 days) | 50 |
| | VV-ETA-S | F-C | 8/8 | 40 | (20 days) | 0 |
| | | F-S | 3/8 | 7.5 | (25 days) | 62.5 |
| | | F-T | 1/8 | 0.87 | (30 days) | 87.5 |
| | VV-ETA-T | F-C | 8/8 | 32 | (20 days) | 0 |
| | | F-S | 1/8 | 0.38 | (25 days) | 87.5 |
| | | F-T | 0/8 | 0 | (30 days) | 100 |
| | | F-S | 10/10 | 11.2 | (20 days) | 0 |
| | | F-T | 10/10 | 25 | (20 days) | 0 |
| | VV-ETA-S | F-S | 9/10 | 16 | (20 days) | 10 |
| | | F-T | 9/10 | 30 | (20 days) | 10 |
| | VV-ETA-T | F-S | 5/10 | 1.7 | (20 days) | 50 |
| | | F-T | 5/10 | 2.8 | (20 days) | 50 |
| Fisher line female rats | VV-O | F-S | 10/10 | 19.6 | (20 days) | 0 |
| | | F-T | 10/10 | 28 | (20 days) | 0 |
| | VV-ETA-S | F-S | 8/10 | 10.6 | (20 days) | 20 |
| | | F-T | 9/9 | 33.8 | (20 days) | 0 |
| | VV-ETA-T | F-S | 5/10 | 0.1 | (25 days) | 50 |
| | | F-T | 1/10 | 90 | | |

Table I shows that, when the animals are subjected to infection with F-S or F-T, the incidence of appearance of tumors in a group of animals treated beforehand using the vaccinia virus VV-ETA-S or VV-ETA-T is lower than in the groups of untreated animals or animals treated with a VV-O vaccinia virus. Moreover, the size of the tumor nodules which appear in animals treated beforehand with VV-ETA-S or VV-ETA-T is much smaller than that of the tumor nodules observed in the untreated animals or animals treated with VV-O.

EXAMPLE 5: Demonstration of the curative effect of H23-ETA

Fisher line rats are infected with tumor cells as described in Example 4. As soon as tumors have appeared (10 to 15 days later), treatment is carried out using the viral preparations, as described in Example 4.

The data and results of the experiment are presented in Table II below:

TABLE II

| | | Number of animals having a tumor nodule relative to the total number of animals treated | | Measured average diameter of the tumors (in mm) | |
|---|---|---|---|---|---|
| Virus | Tumor cells | 25 days after injection | 50 days after injection | 25 days after injection | 50 days after injection |
| VV-O | F-S | 10/10 | 10/10 | 27.8 | all dead |
| | F-T | 10/10 | 10/10 | 27.7 | all dead |
| VV-ETA-S | F-S | 10/10 | 10/10 | 31.5 | all dead |
| | F-T | 9/10 | 7/10 | 15.5 | 8.5 |
| VV-ETA-T | F-S | 9/10 | 10/10 | 26.8 | 50.2 |
| | F-T | 7/10 | 7/10 | 11.6 | 9.4 |

Immunization using VV-ETA-S or VV-ETA-T is effective only in the case of tumors induced with cells expressing the secreted or transmembrane form of H23-ETA. The vaccinal effect of the viruses is hence very specific.

Lastly, the vaccinal effect of VV-ETA-T appears to be superior to that of VV-ETA-S, irrespective of the form of H23-ETA expressed by the cells inducing the tumors.

Table II shows that the treatment of an infection with VV-ETA-S or VV-ETA-T has a favorable effect on the incidence of appearance and the size of the tumors relative to the control test. Moreover, VV-ETA-T appears to be more effective than VV-ETA-S.

SEQUENCE IDENTIFIER Nos. 1 and 2 (SEQ ID NOS: 1 and 2)

Subject: The transmembrane form of the H23-ETA antigen

Sequence type: Sequence of a DNA fragment (SEQ ID NO: 1) and the corresponding amino acid sequence (SEQ ID NO: 2)

Molecule type: Complementary DNA

Origin: Mammary carcinoma line T47D

Characteristics of the complete DNA fragment:
  EcoRI-BalI fragment
  Coding sequence: from nucleotide 58 to nucleotide 1362+(60×n)

Characteristics of the amino acid sequence:
  Signal peptide: from a.a.−21 to a.a.−1
  Mature form: from a.a.1 to a.a. 414*, * denoting [+(20×n)] in which n is a number from 1 to 80
  Repeat sequence: As shown boxed below, in which $X_1$ and $X_2$ are, independently, Pro or Ala and Y is Thr or Asn (SQ ID NO: 3)

```
                GAATTCCCTG GCTGCTTGAA TCTGTTCTGC CCCCTCCCCA CCCATTTCAC   50

CACCACC ATG ACA CCG GGC ACC CAG TCT CCT TTC TTC CTG      90
                        Met Thr Pro Gly Thr Gln Ser Pro Phe Phe Leu
                        -21 -20                 -15

CTG CTG CTC CTC ACA GTG CTT ACA GTT GTT ACA GGT TCT     129
                Leu Leu Leu Leu Thr Val Leu Thr Val Val Thr Gly Ser
                -10             -5                   -1   1

GGT CAT GCA AGC TCT ACC CCA GGT GGA GAA AAG GAG ACT     168
                Gly His Ala Ser Ser Thr Pro Gly Gly Glu Lys Glu Thr
                     5                   10                  15

TCG GCT ACC CAG AGA AGT TCA GTG CCC AGC TCT ACT GAG     207
                Ser Ala Thr Gln Arg Ser Ser Val Pro Ser Ser Thr Glu
                             20                  25

AAG AAT GCT GTG AGT ATG ACC AGC AGC GTA CTC TCC AGC     246
                Lys Asn Ala Val Ser Met Thr Ser Ser Val Leu Ser Ser
                 30                  35                  40

CAC AGC CCC GGT TCA GGC TCC TCC ACC ACT CAG GGA CAG     295
                His Ser Pro Gly Ser Gly Ser Ser Thr Thr Gln Gly Gln
                             45                  50                  55

GAT GTC ACT CTG GCC CCG GCC ACG GAA CCA GCT TCA GGT     324
                Asp Val Thr Leu Ala Pro Ala Thr Glu Pro Ala Ser Gly
                                  60                  65

PvuII
                TCA GCT GCC ACC TGG GGA CAG GAT GTC ACC TCG GTC CCA     363
                Ser Ala Ala Thr Trp Gly Gln Asp Val Thr Ser Val Pro
                 70                  75                  80

GTC ACC AGG CCA GCC CTG GGC TCC ACC ACC CCG CCA GCC     402
                Val Thr Arg Pro Ala Leu Gly Ser Thr Thr Pro Pro Ala
                             85                  90

CAC GAT GTC ACC TCA GCC CCG GAC AAC AAG CCA GCC CCG
                His Asp Val Thr Ser Ala Pro Asp Asn Lys Pro Ala Pro
                 95                  100                 105

┌─────────────────────────────────────────────────────┐
               │ GGC TCC ACC GCC CCC xxx GCC CAC GGT GTC ACC TCG GCC  │
               │ Gly Ser Thr Ala Pro  X₁ Ala His Gly Val Thr Ser Ala │
               │                                                     │
               │ CCG GAC yyy AGG CCG xxx  TTG GGC TCC ACC GCC CCT CCA │
               │ Pro Asp  Y  Ala His  X₂  Leu Gly Ser Thr Ala Pro Pro│
               └─────────────────────────────────────────────────────┘n
                                                              110*

GTC CAC AAT GTC ACC TCG GCC TCA GGC TCT GCA TCA GGC     498 + (60xn)
                Val His Asn Val Thr Ser Ala Ser Gly Ser Ala Ser Gly
                       115*                120*                125

TCA GCT TCT ACT CTG GTG CAC AAC GGC ACC TCT GCC AGG     537 + (60xn)
                Ser Ala Ser Thr Leu Val His Asn Gly Thr Ser Ala Arg
                             130*                135*

GCT ACC ACA ACC CCA GCC AGC AAG AGC ACT CCA CCC AGC     576 + (60xn)
```

-continued

```
                 Ala Thr Thr Thr Pro Ala Ser Lys Ser Thr Pro Phe Ser
                 140*            145*            150*

ATT CCC AGC CAC CAC TCT GAT ACT CCT ACC ACC CTT GCC        615 + (60xn)
Ile Pro Ser His His Ser Asp Thr Pro Thr Thr Leu Ala
        155*            160*            165*

AGC CAT AGC ACC AAG ACT GAT GCC AGT AGC ACT CAC CAT        654 + (60xn)
Ser His Ser Thr Lys Thr Asp Ala Ser Ser Thr His His
                170*            175*

AGC ACG GTA CCT CCT CTC ACC TCC TCC AAT CAC AGC ACT        693 + (60xn)
Ser Thr Val Pro Pro Leu Thr Ser Ser Asn His Ser Thr
        180*            185*            190*

TCT CCC CAG TTG TCT ACT GGG GTC TCT TTC TTT TTC CTG        732 + (60xn)
Ser Pro Gln Leu Ser Thr Gly Val Ser Phe Phe Phe Leu
                195*            200*

TCT TTT CAC ATT TCA AAC CTC CAG TTT AAT TCC TCT CTG        771 + (60xn)
Ser Phe His Ile Ser Asn Leu Gln Phe Asn Ser Ser Leu
205*            210*            215*

PstI
GAA GAT CCC AGC ACC GAC TAC TAC CAA GAG CTG CAG AGA        810 + (60xn)
Glu Asp Pro Ser Thr Asp Tyr Tyr Gln Glu Leu Gln Arg
        220*            225*            230*

GAC ATT TCT GAA ATG TTT TTG CAG ATT TAT AAA CAA GGG        849 + (60xn)
Asp Ile Ser Glu Met Phe Leu Gln Ile Tyr Lys Gln Gly
                235*            240*

GGT TTT CTG GGC CTC TCC AAT ATT AAG TTC AGG CCA GGA5       888 + (60xn)
Gly Phe Leu Gly Leu Ser Asn Ile Lys Phe Arg Pro Gly
        245*            250*            255*

TCT GTG GTG GTA CAA TTG ACT CTG GCC TTC CGA GAA GGT        927 + (60xn)
Ser Val Val Val Gln Leu Thr Leu Ala Phe Arg Glu Gly
                260*            265*

ACC ATC AAT GTC CAC GAC GTG GAG ACA CAG TTC AAT CAG        966 + (60xn)
Thr Ile Asn Val His Asp Val Glu Thr Gln Phe Asn Gln
270*            275*            280*

TAT AAA ACG GAA GCA GCC TCT CGA TAT AAC CTG ACG ATC       1005 + (60xn)
Tyr Lys Thr Glu Ala Ala Ser Arg Tyr Asn Leu Thr Ile
        285*            290*            295*

TCA GAC GTC AGC GTG AGT CAT GTG CCA TTT CCT TTC TCT       1044 + (60xn)
Ser Asp Val Ser Val Ser His Val Pro Phe Pro Phe Ser
                300*            305*

GCC CAG TCT GGG GCT GGG GTG CCA GGC TGG GGC ATC GCG       1083 + (60xn)
Ala Gln Ser Gly Ala Gly Val Pro Gly Trp Gly Ile Ala
        310*            315*            320*

BalI
CTG CTG GTG CTG GTC TGT GTT CTG GTT GCG CTG GCC ATT       1122 + (60xn)
Leu Leu Val Leu Val Cys Val Leu Val Ala Leu Ala Ile
                325*            330*

GTC TAT CTC ATT GCC TTG GCT GTC TGT CAG TGC CGC CGA       1161 + (60xn)
Val Tyr Leu Ile Ala Leu Ala Val Cys Gln Cys Arg Arg
335*            340*            345*

AAG AAC TAC GGG CAG CTG GAC ATC TTT CCA GCC CGG GAT       1200 + (60xn)
Lys Asn Tyr Gly Gln Leu Asp Ile Phe Pro Ala Arg Asp
        350*            355*            360*

ACC TAC CAT CCT ATG AGC GAG TAC CCC ACC TAC CAC ACC       1239 + (60xn)
Thr Tyr His Pro Met Ser Glu Tyr Pro Thr Tyr His Thr
                365*            370*

CAT GGG CGC TAT GTG CCC CCT AGC AGT ACC GAT CGT AGC       1278 + (60xn)
His Gly Arg Tyr Val Pro Pro Ser Ser Thr Asp Arg Ser
        375*            380*            385*

CCC TAT GAG AAG GTT TCT GCA GGT AAT GGT GGC AGC AGC       1317 + (60xn)
Pro Tyr Glu Lys Val Ser Ala Gly Asn Gly Gly Ser Ser
                390*            395*
```

-continued

```
CTC TCT TAC ACA AAC CCA GCA GTG GCA GCC ACT TCT GCC      1356 + (60xn)
Leu Ser Tyr Thr Asn Pro Ala Val Ala Ala Thr Ser Ala
400*                405*                410*

AAC TTG TAG GGGGACGTCG CCCTCTGAGC TGAGTGG                1392 + (60xn)
Asn Leu Ter
```

SEQUENCE IDENTIFIER Nos. 4 and 5 (SEQ ID NOS: 4 and 5)

Subject: The soluble form of the H23-ETA antigen

Sequence type: Sequence of a DNA fragment (SEQ ID NO: 4) and the corresponding amino acid sequence (SEQ ID NO: 5)

Molecule type: Complementary DNA

Origin: Mammary carcinoma line T47D

Characteristics of the complete DNA fragment:

EcoRI-PvuII fragment

Coding sequence: from nucleotide 58 to nucleotide 858+(60×n)

Characteristics of the amino acid sequence:
Signal peptide: from a.a.−21 to a.a.−1
Mature form: from a.a.1 to a.a. 246*, * denoting [+(20×n)] in which n is a number from 1 to 80

Repeat sequence: As shown boxed below, in which $X_1$ and $X_2$ are, independently, Pro or Ala and Y is Thr or Asn (SEQ ID NO: 3)

```
              GAATTCCCTG GCTGCTTGAA TCTGTTCTGC CCCCTCCCCA CCCATTTCAC  50

CACCACC ATG ACA CCG GGC ACC CAG TCT CCT TTC TTC CTG      90
                      Met Thr Pro Gly Thr Gln Ser Pro Phe Phe Leu
                      -21 -20                 -15

CTG CTG CTC CTC ACA GTG CTT ACA GTT GTT ACA GGT TCT     129
              Leu Leu Leu Leu Thr Val Leu Thr Val Val Thr Gly Ser
              -10                 -5                  -1   1

GGT CAT GCA AGC TCT ACC CCA GGT GGA GAA AAG GAG ACT     168
              Gly His Ala Ser Ser Thr Pro Gly Gly Glu Lys Glu Thr
                       5                  10                  15

TCG GCT ACC CAG AGA AGT TCA GTG CCC AGC TCT ACT GAG     207
              Ser Ala Thr Gln Arg Ser Ser Val Pro Ser Ser Thr Glu
                           20                  25

AAG AAT GCT GTG AGT ATG ACC AGC AGC GTA CTC TCC AGC     246
              Lys Asn Ala Val Ser Met Thr Ser Ser Val Leu Ser Ser
               30                  35                  40

CAC AGC CCC GGT TCA GGC TCC TCC ACC ACT CAG GGA CAG     295
              His Ser Pro Gly Ser Gly Ser Ser Thr Thr Gln Gly Gln
                           45                  50                  55

GAT GTC ACT CTG GCC CCG GCC ACG GAA CCA GCT TCA GGT     324
              Asp Val Thr Leu Ala Pro Ala Thr Glu Pro Ala Ser Gly
                                60                  65

PvuII
              TCA GCT GCC ACC TGG GGA CAG GAT GTC ACC TCG GTC CCA     363
              Ser Ala Ala Thr Trp Gly Gln Asp Val Thr Ser Val Pro
                       70                  75                  80

GTC ACC AGG CCA GCC CTG GGC TCC ACC ACC CCG CCA GCC     402
              Val Thr Arg Pro Ala Leu Gly Ser Thr Thr Pro Pro Ala
                           85                  90

CAC GAT GTC ACC TCA GCC CCG GAC AAC AAG CCA GCC |CCG
              His Asp Val Thr Ser Ala Pro Asp Asn Lys Pro Ala |Pro
               95                  100                 105

┌─────────────────────────────────────────────────┐
              │GGC TCC ACC GCC CCC xxx GCC CAC GGT GTC ACC TCG GCC│
              │Gly Ser Thr Ala Pro  X₁ Ala His Gly Val Thr Ser Ala│
              └─────────────────────────────────────────────────┘

┌─────────────────────────────────────────┐
              │CCG GAC yyy AGG CCG xxx│TTG GGC TCC ACC GCC CCT CCA
              │Pro Asp  Y  Ala His X₂ │Leu Gly Ser Thr Ala Pro Pro
              └─────────────────────────────────────────┘ n                  110*

GTC CAC AAT GTC ACC TCG GCC TCA GGC TCT GCA TCA GGC     498 + (60xn)
              Val His Asn Val Thr Ser Ala Ser Gly Ser Ala Ser Gly
```

-continued

```
             115*                 120*                125
TCA GCT TCT ACT CTG GTG CAC AAC GGC ACC TCT GCC AGG      537 + (60xn)
Ser Ala Ser Thr Leu Val His Asn Gly Thr Ser Ala Arg
             130*                 135*

GCT ACC ACA ACC CCA GCC AGC AAG AGC ACT CCA TCC TCA      576 + (60xn)
Ala Thr Thr Thr Pro Ala Ser Lys Ser Thr Pro Phe Ser
140*                 145*                 150*

ATT CCC AGC CAC CAC TCT GAT ACT CCT ACC ACC CTT GCC      615 + (60xn)
Ile Pro Ser His His Ser Asp Thr Pro Thr Thr Leu Ala
             155*                 160*                 165*

AGC CAT AGC ACC AAG ACT GAT GCC AGT AGC ACT CAC CAT      654 + (60xn)
Ser His Ser Thr Lys Thr Asp Ala Ser Ser Thr His His
                 170*                 175*

AGC ACG GTA CCT CCT CTC ACC TCC TCC AAT CAC AGC ACT      693 + (60xn)
Ser Thr Val Pro Pro Leu Thr Ser Ser Asn His Ser Thr
     180*                 185*                 190*

TCT CCC CAG TTG TCT ACT GGG GTC TCT TTC TTT TTC CTG      732 + (60xn)
Ser Pro Gln Leu Ser Thr Gly Val Ser Phe Phe Phe Leu
             195*                 200*

TCT TTT CAC ATT TCA AAC CTC CAG TTT AAT TCC TCT CTG      771 + (60xn)
Ser Phe His Ile Ser Asn Leu Gln Phe Asn Ser Ser Leu
205*                 210*                 215*

GAA GAT CCC AGC ACC GAC TAC TAC CAA GAG CTG CAG AGA      810 + (60xn)
Glu Asp Pro Ser Thr Asp Tyr Tyr Gln Glu Leu Gln Arg
             220*                 225*                 230*

GAC ATT TCT GAA ATG GTG AGT ATC GGC CTT TCC TTC CCC      849 + (60xn)
Asp Ile Ser Glu Met Val Ser Ile Gly Leu Ser Phe Pro
                 235*                 240*

ATG CTC CCC TGA AGGAGCCATC AGAACTGTCC ACACCCTTTG         891
Met Leu Pro Ter
     245*

CATCAAGCCT GAGTCCTTTC CCTCTCACCC CAGTTTTTGC AGATTTATAA   941 + (60xn)

ACAAGGGGGT TTTCTGGGCC TCTCCAATAT TAAGTTCAGG TACAGTTCTG   991 + (60xn)

GGTGTGGACC CAGTGTGGTG GTTGGAGGGT TGGGTGGTGG TCATGACCGT  1041 + (60xn)

AGGAGGGACT GGTCGCACTT AAGGTTGGGG GAAGAGTCGT GAGCCAGAGC  1091 + (60xn)

TGGGACCCGT GGCTGAAGTG CCCATTTCCC TGTGACCAGG CCAGGATCTG  1141 + (60xn)

TGGTGGTACA ATTGACTCTG GCCTTCCGAG AAGGTACCAT CAATGTCCAC  1191 + (60xn)

GACGTGGAGA CACAGTTCAA TCAGTATAAA ACGGAAGCAG CCTCTCGATA  1241 + (60xn)

TAACCTGACG ATCTCAGACG TCAGCGGTGA GGCTACTTCC CTGGCTGCAG  1291 + (60xn)

CCCAGCACCA TGCCGGGGCC CTCTCCTTCC AGTGCCTGGG TCCCCGCTCT  1341 + (60xn)

TTCCTTAGTG CTGGCAGCGG GAGGGCGCC TCCTCTGGGA GACTGCCCTG   1391 + (60xn)

ACCACTGCTT TTCCTTTTAG TGAGTCATGT GCCATTTCCT TTCTCTGCCC  1441 + (60xn

AGTCTGGGGC TGGGGTGCCA GGCTGGGGCA TCGCGCTGCT GGTGCTGGTC  1491 + (60xn)

TGTGTTCTGG TTGCGCTGGC CATTGTCTAT CTCATTGCCT TGGTGAGTGC  1541 + (60xn)

AGTCCCTGGC CCTGATCAGA GCCCCCCGGT AGAAGGCACT CCATGGCCTG  1591 + (60xn)

CCATAACCTC CTATCTCCCC AGGCTGTCTG TCAGTGCCGC CGAAAGAACT  1641 + (60xn)

ACGGGCAG                                                1649 + (60xn)
```

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
       (A) LENGTH: 6192 base pairs
       (B) TYPE: nucleic acid
       (C) STRANDEDNESS: single
       (D) TOPOLOGY: linear (ii) MOLECULE TYPE: DNA (genomic)

(ix) FEATURE:
       (A) NAME/KEY: sig_peptide
       (B) LOCATION: 58..120

(ix) FEATURE:
       (A) NAME/KEY: repeat_region
       (B) LOCATION: 439..5239
       (D) OTHER INFORMATION: /note= "The nucleotides spanning
           439-5239 constitute a repeated region wherein the repeat
           is 60 nucleotides and encodes 20 amino acids, 17 of which
           are fixed. The number of such repeats varies from 1 to
           80."

(ix) FEATURE:
       (A) NAME/KEY: mat_peptide
       (B) LOCATION: 121..6166

(ix) FEATURE:
       (A) NAME/KEY: repeat_region
       (B) LOCATION: 457
       (D) OTHER INFORMATION: /note= "Nucleotide 457 is X1 = NNN
           which is the codon for Pro or Ala wherein Pro = CCT, CCC,
           CCA, or CCG; and Ala = GCT, GCC, GCA, or GCG."

(ix) FEATURE:
       (A) NAME/KEY: repeat_region
       (B) LOCATION: 487
       (D) OTHER INFORMATION: /note= "Nucleotide 487 is Y = NNN
           which is the codon for Thr or Asn wherein Thr = ACT, ACC,
           ACA, or ACG; and Asn = AAT or AAC."

(ix) FEATURE:
       (A) NAME/KEY: repeat_region
       (B) LOCATION: 496
       (D) OTHER INFORMATION: /note= "Nucleotide 496 is X2 = NNN
           which is the codon for Pro or Ala wherein Pro = CCT, CCC,
           CCA, or CCG; and Ala = GCT, GCC, GCA, or GCG."

(xi) SEQUENCE DESCRIPTION: SEQ ID NO:1:

```
GAATTCCCTG GCTGCTTGAA TCTGTTCTGC CCCCTCCCCA CCCATTTCAC CACCACCATG      60

ACACCGGGCA CCCAGTCTCC TTTCTTCCTG CTGCTGCTCC TCACAGTGCT TACAGTTGTT     120

ACAGGTTCTG GTCATGCAAG CTCTACCCCA GGTGGAGAAA AGGAGACTTC GGCTACCCAG     180

AGAAGTTCAG TGCCCAGCTC TACTGAGAAG AATGCTGTGA GTATGACCAG CAGCGTACTC     240

TCCAGCCACA GCCCCGGTTC AGGCTCCTCC ACCACTCAGG GACAGGATGT CACTCTGGCC     300

CCGGCCACGG AACCAGCTTC AGGTTCAGCT GCCACCTGGG GACAGGATGT CACCTCGGTC     360

CCAGTCACCA GGCCAGCCCT GGGCTCCACC ACCCCGCCAG CCCACGATGT CACCTCAGCC     420

CCGGACAACA AGCCAGCCCC GGGCTCCACC GCCCCCNNNG CCCACGGTGT CACCTCGGCC     480

CCGGACNNNA GGCCGNNNCC GGGCTCCACC GCCCCCNNNG CCCACGGTGT CACCTCGGCC     540

CCGGACNNNA GGCCGNNNCC GGGCTCCACC GCCCCCNNNG CCCACGGTGT CACCTCGGCC     600

CCGGACNNNA GGCCGNNNCC GGGCTCCACC GCCCCCNNNG CCCACGGTGT CACCTCGGCC     660
```

-continued

```
CCGGACNNNA GGCCGNNNCC GGGCTCCACC GCCCCCNNNG CCCACGGTGT CACCTCGGCC      720
CCGGACNNNA GGCCGNNNCC GGGCTCCACC GCCCCCNNNG CCCACGGTGT CACCTCGGCC      780
CCGGACNNNA GGCCGNNNCC GGGCTCCACC GCCCCCNNNG CCCACGGTGT CACCTCGGCC      840
CCGGACNNNA GGCCGNNNCC GGGCTCCACC GCCCCCNNNG CCCACGGTGT CACCTCGGCC      900
CCGGACNNNA GGCCGNNNCC GGGCTCCACC GCCCCCNNNG CCCACGGTGT CACCTCGGCC      960
CCGGACNNNA GGCCGNNNCC GGGCTCCACC GCCCCCNNNG CCCACGGTGT CACCTCGGCC     1020
CCGGACNNNA GGCCGNNNCC GGGCTCCACC GCCCCCNNNG CCCACGGTGT CACCTCGGCC     1080
CCGGACNNNA GGCCGNNNCC GGGCTCCACC GCCCCCNNNG CCCACGGTGT CACCTCGGCC     1140
CCGGACNNNA GGCCGNNNCC GGGCTCCACC GCCCCCNNNG CCCACGGTGT CACCTCGGCC     1200
CCGGACNNNA GGCCGNNNCC GGGCTCCACC GCCCCCNNNG CCCACGGTGT CACCTCGGCC     1260
CCGGACNNNA GGCCGNNNCC GGGCTCCACC GCCCCCNNNG CCCACGGTGT CACCTCGGCC     1320
CCGGACNNNA GGCCGNNNCC GGGCTCCACC GCCCCCNNNG CCCACGGTGT CACCTCGGCC     1380
CCGGACNNNA GGCCGNNNCC GGGCTCCACC GCCCCCNNNG CCCACGGTGT CACCTCGGCC     1440
CCGGACNNNA GGCCGNNNCC GGGCTCCACC GCCCCCNNNG CCCACGGTGT CACCTCGGCC     1500
CCGGACNNNA GGCCGNNNCC GGGCTCCACC GCCCCCNNNG CCCACGGTGT CACCTCGGCC     1560
CCGGACNNNA GGCCGNNNCC GGGCTCCACC GCCCCCNNNG CCCACGGTGT CACCTCGGCC     1620
CCGGACNNNA GGCCGNNNCC GGGCTCCACC GCCCCCNNNG CCCACGGTGT CACCTCGGCC     1680
CCGGACNNNA GGCCGNNNCC GGGCTCCACC GCCCCCNNNG CCCACGGTGT CACCTCGGCC     1740
CCGGACNNNA GGCCGNNNCC GGGCTCCACC GCCCCCNNNG CCCACGGTGT CACCTCGGCC     1800
CCGGACNNNA GGCCGNNNCC GGGCTCCACC GCCCCCNNNG CCCACGGTGT CACCTCGGCC     1860
CCGGACNNNA GGCCGNNNCC GGGCTCCACC GCCCCCNNNG CCCACGGTGT CACCTCGGCC     1920
CCGGACNNNA GGCCGNNNCC GGGCTCCACC GCCCCCNNNG CCCACGGTGT CACCTCGGCC     1980
CCGGACNNNA GGCCGNNNCC GGGCTCCACC GCCCCCNNNG CCCACGGTGT CACCTCGGCC     2040
CCGGACNNNA GGCCGNNNCC GGGCTCCACC GCCCCCNNNG CCCACGGTGT CACCTCGGCC     2100
CCGGACNNNA GGCCGNNNCC GGGCTCCACC GCCCCCNNNG CCCACGGTGT CACCTCGGCC     2160
CCGGACNNNA GGCCGNNNCC GGGCTCCACC GCCCCCNNNG CCCACGGTGT CACCTCGGCC     2220
CCGGACNNNA GGCCGNNNCC GGGCTCCACC GCCCCCNNNG CCCACGGTGT CACCTCGGCC     2280
CCGGACNNNA GGCCGNNNCC GGGCTCCACC GCCCCCNNNG CCCACGGTGT CACCTCGGCC     2340
CCGGACNNNA GGCCGNNNCC GGGCTCCACC GCCCCCNNNG CCCACGGTGT CACCTCGGCC     2400
CCGGACNNNA GGCCGNNNCC GGGCTCCACC GCCCCCNNNG CCCACGGTGT CACCTCGGCC     2460
CCGGACNNNA GGCCGNNNCC GGGCTCCACC GCCCCCNNNG CCCACGGTGT CACCTCGGCC     2520
CCGGACNNNA GGCCGNNNCC GGGCTCCACC GCCCCCNNNG CCCACGGTGT CACCTCGGCC     2580
CCGGACNNNA GGCCGNNNCC GGGCTCCACC GCCCCCNNNG CCCACGGTGT CACCTCGGCC     2640
CCGGACNNNA GGCCGNNNCC GGGCTCCACC GCCCCCNNNG CCCACGGTGT CACCTCGGCC     2700
CCGGACNNNA GGCCGNNNCC GGGCTCCACC GCCCCCNNNG CCCACGGTGT CACCTCGGCC     2760
CCGGACNNNA GGCCGNNNCC GGGCTCCACC GCCCCCNNNG CCCACGGTGT CACCTCGGCC     2820
CCGGACNNNA GGCCGNNNCC GGGCTCCACC GCCCCCNNNG CCCACGGTGT CACCTCGGCC     2880
CCGGACNNNA GGCCGNNNCC GGGCTCCACC GCCCCCNNNG CCCACGGTGT CACCTCGGCC     2940
CCGGACNNNA GGCCGNNNCC GGGCTCCACC GCCCCCNNNG CCCACGGTGT CACCTCGGCC     3000
```

-continued

```
CCGGACNNNA GGCCGNNNCC GGGCTCCACC GCCCCCNNNG CCCACGGTGT CACCTCGGCC   3060
CCGGACNNNA GGCCGNNNCC GGGCTCCACC GCCCCCNNNG CCCACGGTGT CACCTCGGCC   3120
CCGGACNNNA GGCCGNNNCC GGGCTCCACC GCCCCCNNNG CCCACGGTGT CACCTCGGCC   3180
CCGGACNNNA GGCCGNNNCC GGGCTCCACC GCCCCCNNNG CCCACGGTGT CACCTCGGCC   3240
CCGGACNNNA GGCCGNNNCC GGGCTCCACC GCCCCCNNNG CCCACGGTGT CACCTCGGCC   3300
CCGGACNNNA GGCCGNNNCC GGGCTCCACC GCCCCCNNNG CCCACGGTGT CACCTCGGCC   3360
CCGGACNNNA GGCCGNNNCC GGGCTCCACC GCCCCCNNNG CCCACGGTGT CACCTCGGCC   3420
CCGGACNNNA GGCCGNNNCC GGGCTCCACC GCCCCCNNNG CCCACGGTGT CACCTCGGCC   3480
CCGGACNNNA GGCCGNNNCC GGGCTCCACC GCCCCCNNNG CCCACGGTGT CACCTCGGCC   3540
CCGGACNNNA GGCCGNNNCC GGGCTCCACC GCCCCCNNNG CCCACGGTGT CACCTCGGCC   3600
CCGGACNNNA GGCCGNNNCC GGGCTCCACC GCCCCCNNNG CCCACGGTGT CACCTCGGCC   3660
CCGGACNNNA GGCCGNNNCC GGGCTCCACC GCCCCCNNNG CCCACGGTGT CACCTCGGCC   3720
CCGGACNNNA GGCCGNNNCC GGGCTCCACC GCCCCCNNNG CCCACGGTGT CACCTCGGCC   3780
CCGGACNNNA GGCCGNNNCC GGGCTCCACC GCCCCCNNNG CCCACGGTGT CACCTCGGCC   3840
CCGGACNNNA GGCCGNNNCC GGGCTCCACC GCCCCCNNNG CCCACGGTGT CACCTCGGCC   3900
CCGGACNNNA GGCCGNNNCC GGGCTCCACC GCCCCCNNNG CCCACGGTGT CACCTCGGCC   3960
CCGGACNNNA GGCCGNNNCC GGGCTCCACC GCCCCCNNNG CCCACGGTGT CACCTCGGCC   4020
CCGGACNNNA GGCCGNNNCC GGGCTCCACC GCCCCCNNNG CCCACGGTGT CACCTCGGCC   4080
CCGGACNNNA GGCCGNNNCC GGGCTCCACC GCCCCCNNNG CCCACGGTGT CACCTCGGCC   4140
CCGGACNNNA GGCCGNNNCC GGGCTCCACC GCCCCCNNNG CCCACGGTGT CACCTCGGCC   4200
CCGGACNNNA GGCCGNNNCC GGGCTCCACC GCCCCCNNNG CCCACGGTGT CACCTCGGCC   4260
CCGGACNNNA GGCCGNNNCC GGGCTCCACC GCCCCCNNNG CCCACGGTGT CACCTCGGCC   4320
CCGGACNNNA GGCCGNNNCC GGGCTCCACC GCCCCCNNNG CCCACGGTGT CACCTCGGCC   4380
CCGGACNNNA GGCCGNNNCC GGGCTCCACC GCCCCCNNNG CCCACGGTGT CACCTCGGCC   4440
CCGGACNNNA GGCCGNNNCC GGGCTCCACC GCCCCCNNNG CCCACGGTGT CACCTCGGCC   4500
CCGGACNNNA GGCCGNNNCC GGGCTCCACC GCCCCCNNNG CCCACGGTGT CACCTCGGCC   4560
CCGGACNNNA GGCCGNNNCC GGGCTCCACC GCCCCCNNNG CCCACGGTGT CACCTCGGCC   4620
CCGGACNNNA GGCCGNNNCC GGGCTCCACC GCCCCCNNNG CCCACGGTGT CACCTCGGCC   4680
CCGGACNNNA GGCCGNNNCC GGGCTCCACC GCCCCCNNNG CCCACGGTGT CACCTCGGCC   4740
CCGGACNNNA GGCCGNNNCC GGGCTCCACC GCCCCCNNNG CCCACGGTGT CACCTCGGCC   4800
CCGGACNNNA GGCCGNNNCC GGGCTCCACC GCCCCCNNNG CCCACGGTGT CACCTCGGCC   4860
CCGGACNNNA GGCCGNNNCC GGGCTCCACC GCCCCCNNNG CCCACGGTGT CACCTCGGCC   4920
CCGGACNNNA GGCCGNNNCC GGGCTCCACC GCCCCCNNNG CCCACGGTGT CACCTCGGCC   4980
CCGGACNNNA GGCCGNNNCC GGGCTCCACC GCCCCCNNNG CCCACGGTGT CACCTCGGCC   5040
CCGGACNNNA GGCCGNNNCC GGGCTCCACC GCCCCCNNNG CCCACGGTGT CACCTCGGCC   5100
CCGGACNNNA GGCCGNNNCC GGGCTCCACC GCCCCCNNNG CCCACGGTGT CACCTCGGCC   5160
CCGGACNNNA GGCCGNNNCC GGGCTCCACC GCCCCCNNNG CCCACGGTGT CACCTCGGCC   5220
CCGGACNNNA GGCCGNNNTT GGGCTCCACC GCCCCTCCAG TCCACAATGT CACCTCGGCC   5280
TCAGGCTCTG CATCAGGCTC AGCTTCTACT CTGGTGCACA ACGGCACCTC TGCCAGGGCT   5340
ACCACAACCC CAGCCAGCAA GAGCACTCCA CCCAGCATTC CCAGCCACCA CTCTGATACT   5400
```

```
CCTACCACCC TTGCCAGCCA TAGCACCAAG ACTGATGCCA GTAGCACTCA CCATAGCACG      5460

GTACCTCCTC TCACCTCCTC CAATCACAGC ACTTCTCCCC AGTTGTCTAC TGGGGTCTCT      5520

TTCTTTTTCC TGTCTTTTCA CATTTCAAAC CTCCAGTTTA ATTCCTCTCT GGAAGATCCC      5580

AGCACCGACT ACTACCAAGA GCTGCAGAGA GACATTTCTG AAATGTTTTT GCAGAATTAT      5640

AAACAAGGGG GTTTTCTGGG CCTCTCCAAT ATTAAGTTCA GGCCAGAATC TGTGGTGGTA      5700

CAATTGACTC TGGCCTTCCG AGAAGGTACC ATCAATGTCC ACGACGTGGA GACACAGTTC      5760

AATCAGTATA AAACGGAAGC AGCCTCTCGA TATAACCTGA CGATCTCAGA CGTCAGCGTG      5820

AGTCATGTGC CATTTCCTTT CTCTGCCCAG TCTGGGGCTG GGGTGCCAGG CTGGGGCATC      5880

GCGCTGCTGG TGCTGGTCTG TGTTCTGGTT GCGCTGGCCA TTGTCTATCT CATTGCCTTG      5940

GCTGTCTGTC AGTGCCGCCG AAAGAACTAC GGGCAGCTGG ACATCTTTCC AGCCCGGGAT      6000

ACCTACCATC CTATGAGCGA GTACCCCACC TACCACACCC ATGGGCGCTA TGTGCCCCCT      6060

AGCAGTACCG ATCGTAGCCC CTATGAGAAG GTTTCTGCAG GTAATGGTGG CAGCAGCCTC      6120

TCTTACACAA ACCCAGCAGT GGCAGCCACT TCTGCCAACT TGTAGGGGCA CGTCGCCCTC      6180

TGAGCTGAGT GG                                                        6192

(2) INFORMATION FOR SEQ ID NO:2:

(i) SEQUENCE CHARACTERISTICS:
        (A) LENGTH: 2035 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 128..1899
        (D) OTHER INFORMATION: /note= "The amino acids spanning
            128 to 1899 constitute a repeated region wherein the
            repeat is 20 amino acids, 17 of which are fixed. The
            number of such repeats varies from 1 to 40."

(ix) FEATURE:
        (A) NAME/KEY: Peptide
        (B) LOCATION: 134
        (D) OTHER INFORMATION: /note= "Amino acid 134 is X1 = Xaa
            Xaa Xaa which is the codon for Pro or Ala wherein Pro =
            CCT, CCC, CCA, or CCG; and Ala = GCT, GCC, GCA, or GCG."

(ix) FEATURE:
        (A) NAME/KEY: Peptide
        (B) LOCATION: 144
        (D) OTHER INFORMATION: /note= "Amino acid 144 is Y = Xaa
            which is the codon for Thr or Asn wherein Thr = ACT, ACC,
            ACA, or ACG; and Asn = AAT or AAC."

(ix) FEATURE:
        (A) NAME/KEY: Peptide
        (B) LOCATION: 147
        (D) OTHER INFORMATION: /note= "Amino acid 147 is X2 = Xaa
            which is the codon for Pro or Ala wherein Pro = CCT, CCC,
            CCA, or CCG; and Ala = GCT, GCC, GCA, or GCG."

(ix) FEATURE:
        (A) NAME/KEY: Peptide
        (B) LOCATION: 1..21
        (D) OTHER INFORMATION: /note= "Amino acids 1 to 21 are a
            21 amino acid precursor sequence."

(xi) SEQUENCE DESCRIPTION: SEQ ID NO:2:

Met Thr Pro Gly Thr Gln Ser Pro Phe Phe Leu Leu Leu Leu Leu Thr
1               5                   10                  15
```

```
Val Leu Thr Val Val Thr Gly Ser Gly His Ala Ser Ser Thr Pro Gly
             20                  25                  30

Gly Glu Lys Glu Thr Ser Ala Thr Gln Arg Ser Ser Val Pro Ser Ser
             35                  40                  45

Thr Glu Lys Asn Ala Val Ser Met Thr Ser Ser Val Leu Ser Ser His
 50                  55                  60

Ser Pro Gly Ser Gly Ser Ser Thr Thr Gln Gly Gln Asp Val Thr Leu
 65                  70                  75                  80

Ala Pro Ala Thr Glu Pro Ala Ser Gly Ser Ala Ala Thr Trp Gly Gln
                 85                  90                  95

Asp Val Thr Ser Val Pro Val Thr Arg Pro Ala Leu Gly Ser Thr Thr
                100                 105                 110

Pro Pro Ala His Asp Val Thr Ser Ala Pro Asp Asn Lys Pro Ala Pro
                115                 120                 125

Gly Ser Thr Ala Pro Xaa Ala His Gly Val Thr Ser Ala Pro Asp Xaa
             130                 135                 140

Arg Pro Xaa Pro Gly Ser Thr Ala Pro Xaa Ala His Gly Val Thr Ser
145                 150                 155                 160

Ala Pro Asp Xaa Arg Pro Xaa Pro Gly Ser Thr Ala Pro Xaa Ala His
                165                 170                 175

Gly Val Thr Ser Ala Pro Asp Xaa Arg Pro Xaa Pro Gly Ser Thr Ala
                180                 185                 190

Pro Xaa Ala His Gly Val Thr Ser Ala Pro Asp Xaa Arg Pro Xaa Pro
         195                 200                 205

Gly Ser Thr Ala Pro Xaa Ala His Gly Val Thr Ser Ala Pro Asp Xaa
             210                 215                 220

Arg Pro Xaa Pro Gly Ser Thr Ala Pro Xaa Ala His Gly Val Thr Ser
225                 230                 235                 240

Ala Pro Asp Xaa Arg Pro Xaa Pro Gly Ser Thr Ala Pro Xaa Ala His
                245                 250                 255

Gly Val Thr Ser Ala Pro Asp Xaa Arg Pro Xaa Pro Gly Ser Thr Ala
                260                 265                 270

Pro Xaa Ala His Gly Val Thr Ser Ala Pro Asp Xaa Arg Pro Xaa Pro
         275                 280                 285

Gly Ser Thr Ala Pro Xaa Ala His Gly Val Thr Ser Ala Pro Asp Xaa
             290                 295                 300

Arg Pro Xaa Pro Gly Ser Thr Ala Pro Xaa Ala His Gly Val Thr Ser
305                 310                 315                 320

Ala Pro Asp Xaa Arg Pro Xaa Pro Gly Ser Thr Ala Pro Xaa Ala His
                325                 330                 335

Gly Val Thr Ser Ala Pro Asp Xaa Arg Pro Xaa Pro Gly Ser Thr Ala
                340                 345                 350

Pro Xaa Ala His Gly Val Thr Ser Ala Pro Asp Xaa Arg Pro Xaa Pro
         355                 360                 365

Gly Ser Thr Ala Pro Xaa Ala His Gly Val Thr Ser Ala Pro Asp Xaa
             370                 375                 380

Arg Pro Xaa Pro Gly Ser Thr Ala Pro Xaa Ala His Gly Val Thr Ser
385                 390                 395                 400

Ala Pro Asp Xaa Arg Pro Xaa Pro Gly Ser Thr Ala Pro Xaa Ala His
                405                 410                 415

Gly Val Thr Ser Ala Pro Asp Xaa Arg Pro Xaa Pro Gly Ser Thr Ala
                420                 425                 430
```

```
Pro Xaa Ala His Gly Val Thr Ser Ala Pro Asp Xaa Arg Pro Xaa Pro
    435                 440                 445

Gly Ser Thr Ala Pro Xaa Ala His Gly Val Thr Ser Ala Pro Asp Xaa
450                 455                 460

Arg Pro Xaa Pro Gly Ser Thr Ala Pro Xaa Ala His Gly Val Thr Ser
465                 470                 475                 480

Ala Pro Asp Xaa Arg Pro Xaa Pro Gly Ser Thr Ala Pro Xaa Ala His
            485                 490                 495

Gly Val Thr Ser Ala Pro Asp Xaa Arg Pro Xaa Pro Gly Ser Thr Ala
                500                 505                 510

Pro Xaa Ala His Gly Val Thr Ser Ala Pro Asp Xaa Arg Pro Xaa Pro
    515                 520                 525

Gly Ser Thr Ala Pro Xaa Ala His Gly Val Thr Ser Ala Pro Asp Xaa
530                 535                 540

Arg Pro Xaa Pro Gly Ser Thr Ala Pro Xaa Ala His Gly Val Thr Ser
545                 550                 555                 560

Ala Pro Asp Xaa Arg Pro Xaa Pro Gly Ser Thr Ala Pro Xaa Ala His
            565                 570                 575

Gly Val Thr Ser Ala Pro Asp Xaa Arg Pro Xaa Pro Gly Ser Thr Ala
                580                 585                 590

Pro Xaa Ala His Gly Val Thr Ser Ala Pro Asp Xaa Arg Pro Xaa Pro
    595                 600                 605

Gly Ser Thr Ala Pro Xaa Ala His Gly Val Thr Ser Ala Pro Asp Xaa
610                 615                 620

Arg Pro Xaa Pro Gly Ser Thr Ala Pro Xaa Ala His Gly Val Thr Ser
625                 630                 635                 640

Ala Pro Asp Xaa Arg Pro Xaa Pro Gly Ser Thr Ala Pro Xaa Ala His
            645                 650                 655

Gly Val Thr Ser Ala Pro Asp Xaa Arg Pro Xaa Pro Gly Ser Thr Ala
                660                 665                 670

Pro Xaa Ala His Gly Val Thr Ser Ala Pro Asp Xaa Arg Pro Xaa Pro
    675                 680                 685

Gly Ser Thr Ala Pro Xaa Ala His Gly Val Thr Ser Ala Pro Asp Xaa
690                 695                 700

Arg Pro Xaa Pro Gly Ser Thr Ala Pro Xaa Ala His Gly Val Thr Ser
705                 710                 715                 720

Ala Pro Asp Xaa Arg Pro Xaa Pro Gly Ser Thr Ala Pro Xaa Ala His
            725                 730                 735

Gly Val Thr Ser Ala Pro Asp Xaa Arg Pro Xaa Pro Gly Ser Thr Ala
                740                 745                 750

Pro Xaa Ala His Gly Val Thr Ser Ala Pro Asp Xaa Arg Pro Xaa Pro
    755                 760                 765

Gly Ser Thr Ala Pro Xaa Ala His Gly Val Thr Ser Ala Pro Asp Xaa
770                 775                 780

Arg Pro Xaa Pro Gly Ser Thr Ala Pro Xaa Ala His Gly Val Thr Ser
785                 790                 795                 800

Ala Pro Asp Xaa Arg Pro Xaa Pro Gly Ser Thr Ala Pro Xaa Ala His
            805                 810                 815

Gly Val Thr Ser Ala Pro Asp Xaa Arg Pro Xaa Pro Gly Ser Thr Ala
                820                 825                 830

Pro Xaa Ala His Gly Val Thr Ser Ala Pro Asp Xaa Arg Pro Xaa Pro
    835                 840                 845

Gly Ser Thr Ala Pro Xaa Ala His Gly Val Thr Ser Ala Pro Asp Xaa
```

-continued

```
            850                 855                 860
Arg Pro Xaa Pro Gly Ser Thr Ala Pro Xaa Ala His Gly Val Thr Ser
865                 870                 875                 880
Ala Pro Asp Xaa Arg Pro Xaa Pro Gly Ser Thr Ala Pro Xaa Ala His
                885                 890                 895
Gly Val Thr Ser Ala Pro Asp Xaa Arg Pro Xaa Pro Gly Ser Thr Ala
            900                 905                 910
Pro Xaa Ala His Gly Val Thr Ser Ala Pro Asp Xaa Arg Pro Xaa Pro
        915                 920                 925
Gly Ser Thr Ala Pro Xaa Ala His Gly Val Thr Ser Ala Pro Asp Xaa
    930                 935                 940
Arg Pro Xaa Pro Gly Ser Thr Ala Pro Xaa Ala His Gly Val Thr Ser
945                 950                 955                 960
Ala Pro Asp Xaa Arg Pro Xaa Pro Gly Ser Thr Ala Pro Xaa Ala His
                965                 970                 975
Gly Val Thr Ser Ala Pro Asp Xaa Arg Pro Xaa Pro Gly Ser Thr Ala
            980                 985                 990
Pro Xaa Ala His Gly Val Thr Ser Ala Pro Asp Xaa Arg Pro Xaa Pro
        995                 1000                1005
Gly Ser Thr Ala Pro Xaa Ala His Gly Val Thr Ser Ala Pro Asp Xaa
    1010                1015                1020
Arg Pro Xaa Pro Gly Ser Thr Ala Pro Xaa Ala His Gly Val Thr Ser
1025                1030                1035                1040
Ala Pro Asp Xaa Arg Pro Xaa Pro Gly Ser Thr Ala Pro Xaa Ala His
                1045                1050                1055
Gly Val Thr Ser Ala Pro Asp Xaa Arg Pro Xaa Pro Gly Ser Thr Ala
            1060                1065                1070
Pro Xaa Ala His Gly Val Thr Ser Ala Pro Asp Xaa Arg Pro Xaa Pro
        1075                1080                1085
Gly Ser Thr Ala Pro Xaa Ala His Gly Val Thr Ser Ala Pro Asp Xaa
    1090                1095                1100
Arg Pro Xaa Pro Gly Ser Thr Ala Pro Xaa Ala His Gly Val Thr Ser
1105                1110                1115                1120
Ala Pro Asp Xaa Arg Pro Xaa Pro Gly Ser Thr Ala Pro Xaa Ala His
                1125                1130                1135
Gly Val Thr Ser Ala Pro Asp Xaa Arg Pro Xaa Pro Gly Ser Thr Ala
            1140                1145                1150
Pro Xaa Ala His Gly Val Thr Ser Ala Pro Asp Xaa Arg Pro Xaa Pro
        1155                1160                1165
Gly Ser Thr Ala Pro Xaa Ala His Gly Val Thr Ser Ala Pro Asp Xaa
    1170                1175                1180
Arg Pro Xaa Pro Gly Ser Thr Ala Pro Xaa Ala His Gly Val Thr Ser
1185                1190                1195                1200
Ala Pro Asp Xaa Arg Pro Xaa Pro Gly Ser Thr Ala Pro Xaa Ala His
                1205                1210                1215
Gly Val Thr Ser Ala Pro Asp Xaa Arg Pro Xaa Pro Gly Ser Thr Ala
            1220                1225                1230
Pro Xaa Ala His Gly Val Thr Ser Ala Pro Asp Xaa Arg Pro Xaa Pro
        1235                1240                1245
Gly Ser Thr Ala Pro Xaa Ala His Gly Val Thr Ser Ala Pro Asp Xaa
    1250                1255                1260
Arg Pro Xaa Pro Gly Ser Thr Ala Pro Xaa Ala His Gly Val Thr Ser
1265                1270                1275                1280
```

-continued

```
Ala Pro Asp Xaa Arg Pro Xaa Pro Gly Ser Thr Ala Pro Xaa Ala His
            1285                1290                1295
Gly Val Thr Ser Ala Pro Asp Xaa Arg Pro Xaa Pro Gly Ser Thr Ala
        1300                1305                1310
Pro Xaa Ala His Gly Val Thr Ser Ala Pro Asp Xaa Arg Pro Xaa Pro
    1315                1320                1325
Gly Ser Thr Ala Pro Xaa Ala His Gly Val Thr Ser Ala Pro Asp Xaa
        1330                1335                1340
Arg Pro Xaa Pro Gly Ser Thr Ala Pro Xaa Ala His Gly Val Thr Ser
1345                1350                1355                1360
Ala Pro Asp Xaa Arg Pro Xaa Pro Gly Ser Thr Ala Pro Xaa Ala His
            1365                1370                1375
Gly Val Thr Ser Ala Pro Asp Xaa Arg Pro Xaa Pro Gly Ser Thr Ala
        1380                1385                1390
Pro Xaa Ala His Gly Val Thr Ser Ala Pro Asp Xaa Arg Pro Xaa Pro
    1395                1400                1405
Gly Ser Thr Ala Pro Xaa Ala His Gly Val Thr Ser Ala Pro Asp Xaa
        1410                1415                1420
Arg Pro Xaa Pro Gly Ser Thr Ala Pro Xaa Ala His Gly Val Thr Ser
1425                1430                1435                1440
Ala Pro Asp Xaa Arg Pro Xaa Pro Gly Ser Thr Ala Pro Xaa Ala His
            1445                1450                1455
Gly Val Thr Ser Ala Pro Asp Xaa Arg Pro Xaa Pro Gly Ser Thr Ala
        1460                1465                1470
Pro Xaa Ala His Gly Val Thr Ser Ala Pro Asp Xaa Arg Pro Xaa Pro
    1475                1480                1485
Gly Ser Thr Ala Pro Xaa Ala His Gly Val Thr Ser Ala Pro Asp Xaa
        1490                1495                1500
Arg Pro Xaa Pro Gly Ser Thr Ala Pro Xaa Ala His Gly Val Thr Ser
1505                1510                1515                1520
Ala Pro Asp Xaa Arg Pro Xaa Pro Gly Ser Thr Ala Pro Xaa Ala His
            1525                1530                1535
Gly Val Thr Ser Ala Pro Asp Xaa Arg Pro Xaa Pro Gly Ser Thr Ala
        1540                1545                1550
Pro Xaa Ala His Gly Val Thr Ser Ala Pro Asp Xaa Arg Pro Xaa Pro
    1555                1560                1565
Gly Ser Thr Ala Pro Xaa Ala His Gly Val Thr Ser Ala Pro Asp Xaa
        1570                1575                1580
Arg Pro Xaa Pro Gly Ser Thr Ala Pro Xaa Ala His Gly Val Thr Ser
1585                1590                1595                1600
Ala Pro Asp Xaa Arg Pro Xaa Pro Gly Ser Thr Ala Pro Xaa Ala His
            1605                1610                1615
Gly Val Thr Ser Ala Pro Asp Xaa Arg Pro Xaa Pro Gly Ser Thr Ala
        1620                1625                1630
Pro Xaa Ala His Gly Val Thr Ser Ala Pro Asp Xaa Arg Pro Xaa Pro
    1635                1640                1645
Gly Ser Thr Ala Pro Xaa Ala His Gly Val Thr Ser Ala Pro Asp Xaa
        1650                1655                1660
Arg Pro Xaa Pro Gly Ser Thr Ala Pro Xaa Ala His Gly Val Thr Ser
1665                1670                1675                1680
Ala Pro Asp Xaa Arg Pro Xaa Pro Gly Ser Thr Ala Pro Xaa Ala His
            1685                1690                1695
```

-continued

```
Gly Val Thr Ser Ala Pro Asp Xaa Arg Pro Xaa Pro Gly Ser Thr Ala
            1700                1705                1710

Pro Xaa Ala His Gly Val Thr Ser Ala Pro Asp Xaa Arg Pro Xaa Leu
        1715                1720                1725

Gly Ser Thr Ala Pro Pro Val His Asn Val Thr Ser Ala Ser Gly Ser
    1730                1735                1740

Ala Ser Gly Ser Ala Ser Thr Leu Val His Asn Gly Thr Ser Ala Arg
1745                1750                1755                1760

Ala Thr Thr Thr Pro Ala Ser Lys Ser Thr Pro Pro Ser Ile Pro Ser
                1765                1770                1775

His His Ser Asp Thr Pro Thr Thr Leu Ala Ser His Ser Thr Lys Thr
            1780                1785                1790

Asp Ala Ser Ser Thr His His Ser Thr Val Pro Pro Leu Thr Ser Ser
        1795                1800                1805

Asn His Ser Thr Ser Pro Gln Leu Ser Thr Gly Val Ser Phe Phe Phe
    1810                1815                1820

Leu Ser Phe His Ile Ser Asn Leu Gln Phe Asn Ser Ser Leu Glu Asp
1825                1830                1835                1840

Pro Ser Thr Asp Tyr Tyr Gln Glu Leu Gln Arg Asp Ile Ser Glu Met
                1845                1850                1855

Phe Leu Gln Asn Tyr Lys Gln Gly Gly Phe Leu Gly Leu Ser Asn Ile
            1860                1865                1870

Lys Phe Arg Pro Glu Ser Val Val Gln Leu Thr Leu Ala Phe Arg
        1875                1880                1885

Glu Gly Thr Ile Asn Val His Asp Val Glu Thr Gln Phe Asn Gln Tyr
    1890                1895                1900

Lys Thr Glu Ala Ala Ser Arg Tyr Asn Leu Thr Ile Ser Asp Val Ser
1905                1910                1915                1920

Val Ser His Val Pro Phe Pro Phe Ser Ala Gln Ser Gly Ala Gly Val
                1925                1930                1935

Pro Gly Trp Gly Ile Ala Leu Leu Val Leu Val Cys Val Leu Val Ala
            1940                1945                1950

Leu Ala Ile Val Tyr Leu Ile Ala Leu Ala Val Cys Gln Cys Arg Arg
        1955                1960                1965

Lys Asn Tyr Gly Gln Leu Asp Ile Phe Pro Ala Arg Asp Thr Tyr His
    1970                1975                1980

Pro Met Ser Glu Tyr Pro Thr Tyr His Thr His Gly Arg Tyr Val Pro
1985                1990                1995                2000

Pro Ser Ser Thr Asp Arg Ser Pro Tyr Glu Lys Val Ser Ala Gly Asn
                2005                2010                2015

Gly Gly Ser Ser Leu Ser Tyr Thr Asn Pro Ala Val Ala Ala Thr Ser
            2020                2025                2030

Ala Asn Leu
    2035
```

(2) INFORMATION FOR SEQ ID NO:3:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide

```
            (B) LOCATION: 7..20
            (D) OTHER INFORMATION: /note= "Xaa at positions 7 and 20
                is X which is Pro or Ala."

(ix) FEATURE:
            (A) NAME/KEY: Peptide
            (B) LOCATION: 12
            (D) OTHER INFORMATION: /note= "Xaa at position 12 is Y
                which is Thr or Asn."

(xi) SEQUENCE DESCRIPTION: SEQ ID NO:3:

Pro Gly Ser Thr Ala Pro Xaa Ala His Gly Val Thr Ser Ala Pro Asp
1               5                   10                  15

Xaa Arg Pro Xaa
            20

(2) INFORMATION FOR SEQ ID NO:4:

(i) SEQUENCE CHARACTERISTICS:
            (A) LENGTH: 6449 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: sig_peptide
            (B) LOCATION: 58..120

(ix) FEATURE:
            (A) NAME/KEY: repeat_region
            (B) LOCATION: 439..5239
            (D) OTHER INFORMATION: /note= "The nucleotides spanning
                439-5239 constitute a repeated region wherein the repeat
                is 60 nucleotides and encodes 20 amino acids, 17 of which
                are fixed. The number of such repeats varies from 1 to
                80."

(ix) FEATURE:
            (A) NAME/KEY: mat_peptide
            (B) LOCATION: 121..5661

(ix) FEATURE:
            (A) NAME/KEY: repeat_region
            (B) LOCATION: 457
            (D) OTHER INFORMATION: /note= "Nucleotide 457 is X1 = NNN
                which is the codon for Pro or Ala wherein Pro = CCT, CCC,
                CCA, or CCG; and Ala = GCT, GCC, GCA, or GCG."

(ix) FEATURE:
            (A) NAME/KEY: repeat_region
            (B) LOCATION: 487
            (D) OTHER INFORMATION: /note= "Nucleotide 487 is Y = NNN
                which is the codon for Thr or Asn wherein Thr = ACT, ACC,
                ACA, or ACG; and Asn = AAT or AAC."

(ix) FEATURE:
            (A) NAME/KEY: repeat_region
            (B) LOCATION: 496
            (D) OTHER INFORMATION: /note= "Nucleotide 496 is X2 = NNN
                which is the codon for Pro or Ala wherein Pro = CCT, CCC,
                CCA, or CCG; and Ala = GCT, GCC, GCA, or GCG."

(xi) SEQUENCE DESCRIPTION: SEQ ID NO:4:

GAATTCCCTG GCTGCTTGAA TCTGTTCTGC CCCCTCCCCA CCCATTTCAC CACCACCATG      60

ACACCGGGCA CCCAGTCTCC TTTCTTCCTG CTGCTGCTCC TCACAGTGCT TACAGTTGTT    120

ACAGGTTCTG GTCATGCAAG CTCTACCCCA GGTGGAGAAA AGGAGACTTC GGCTACCCAG    180

AGAAGTTCAG TGCCCAGCTC TACTGAGAAG AATGCTGTGA GTATGACCAG CAGCGTACTC    240

TCCAGCCACA GCCCCGGTTC AGGCTCCTCC ACCACTCAGG GACAGGATGT CACTCTGGCC    300
```

-continued

```
CCGGCCACGG AACCAGCTTC AGGTTCAGCT GCCACCTGGG GACAGGATGT CACCTCGGTC    360

CCAGTCACCA GGCCAGCCCT GGGCTCCACC ACCCCGCCAG CCCACGATGT CACCTCAGCC    420

CCGGACAACA AGCCAGCCCC GGGCTCCACC GCCCCCNNNG CCCACGGTGT CACCTCGGCC    480

CCGGACNNNA GGCCGNNNCC GGGCTCCACC GCCCCCNNNG CCCACGGTGT CACCTCGGCC    540

CCGGACNNNA GGCCGNNNCC GGGCTCCACC GCCCCCNNNG CCCACGGTGT CACCTCGGCC    600

CCGGACNNNA GGCCGNNNCC GGGCTCCACC GCCCCCNNNG CCCACGGTGT CACCTCGGCC    660

CCGGACNNNA GGCCGNNNCC GGGCTCCACC GCCCCCNNNG CCCACGGTGT CACCTCGGCC    720

CCGGACNNNA GGCCGNNNCC GGGCTCCACC GCCCCCNNNG CCCACGGTGT CACCTCGGCC    780

CCGGACNNNA GGCCGNNNCC GGGCTCCACC GCCCCCNNNG CCCACGGTGT CACCTCGGCC    840

CCGGACNNNA GGCCGNNNCC GGGCTCCACC GCCCCCNNNG CCCACGGTGT CACCTCGGCC    900

CCGGACNNNA GGCCGNNNCC GGGCTCCACC GCCCCCNNNG CCCACGGTGT CACCTCGGCC    960

CCGGACNNNA GGCCGNNNCC GGGCTCCACC GCCCCCNNNG CCCACGGTGT CACCTCGGCC   1020

CCGGACNNNA GGCCGNNNCC GGGCTCCACC GCCCCCNNNG CCCACGGTGT CACCTCGGCC   1080

CCGGACNNNA GGCCGNNNCC GGGCTCCACC GCCCCCNNNG CCCACGGTGT CACCTCGGCC   1140

CCGGACNNNA GGCCGNNNCC GGGCTCCACC GCCCCCNNNG CCCACGGTGT CACCTCGGCC   1200

CCGGACNNNA GGCCGNNNCC GGGCTCCACC GCCCCCNNNG CCCACGGTGT CACCTCGGCC   1260

CCGGACNNNA GGCCGNNNCC GGGCTCCACC GCCCCCNNNG CCCACGGTGT CACCTCGGCC   1320

CCGGACNNNA GGCCGNNNCC GGGCTCCACC GCCCCCNNNG CCCACGGTGT CACCTCGGCC   1380

CCGGACNNNA GGCCGNNNCC GGGCTCCACC GCCCCCNNNG CCCACGGTGT CACCTCGGCC   1440

CCGGACNNNA GGCCGNNNCC GGGCTCCACC GCCCCCNNNG CCCACGGTGT CACCTCGGCC   1500

CCGGACNNNA GGCCGNNNCC GGGCTCCACC GCCCCCNNNG CCCACGGTGT CACCTCGGCC   1560

CCGGACNNNA GGCCGNNNCC GGGCTCCACC GCCCCCNNNG CCCACGGTGT CACCTCGGCC   1620

CCGGACNNNA GGCCGNNNCC GGGCTCCACC GCCCCCNNNG CCCACGGTGT CACCTCGGCC   1680

CCGGACNNNA GGCCGNNNCC GGGCTCCACC GCCCCCNNNG CCCACGGTGT CACCTCGGCC   1740

CCGGACNNNA GGCCGNNNCC GGGCTCCACC GCCCCCNNNG CCCACGGTGT CACCTCGGCC   1800

CCGGACNNNA GGCCGNNNCC GGGCTCCACC GCCCCCNNNG CCCACGGTGT CACCTCGGCC   1860

CCGGACNNNA GGCCGNNNCC GGGCTCCACC GCCCCCNNNG CCCACGGTGT CACCTCGGCC   1920

CCGGACNNNA GGCCGNNNCC GGGCTCCACC GCCCCCNNNG CCCACGGTGT CACCTCGGCC   1980

CCGGACNNNA GGCCGNNNCC GGGCTCCACC GCCCCCNNNG CCCACGGTGT CACCTCGGCC   2040

CCGGACNNNA GGCCGNNNCC GGGCTCCACC GCCCCCNNNG CCCACGGTGT CACCTCGGCC   2100

CCGGACNNNA GGCCGNNNCC GGGCTCCACC GCCCCCNNNG CCCACGGTGT CACCTCGGCC   2160

CCGGACNNNA GGCCGNNNCC GGGCTCCACC GCCCCCNNNG CCCACGGTGT CACCTCGGCC   2220

CCGGACNNNA GGCCGNNNCC GGGCTCCACC GCCCCCNNNG CCCACGGTGT CACCTCGGCC   2280

CCGGACNNNA GGCCGNNNCC GGGCTCCACC GCCCCCNNNG CCCACGGTGT CACCTCGGCC   2340

CCGGACNNNA GGCCGNNNCC GGGCTCCACC GCCCCCNNNG CCCACGGTGT CACCTCGGCC   2400

CCGGACNNNA GGCCGNNNCC GGGCTCCACC GCCCCCNNNG CCCACGGTGT CACCTCGGCC   2460

CCGGACNNNA GGCCGNNNCC GGGCTCCACC GCCCCCNNNG CCCACGGTGT CACCTCGGCC   2520

CCGGACNNNA GGCCGNNNCC GGGCTCCACC GCCCCCNNNG CCCACGGTGT CACCTCGGCC   2580

CCGGACNNNA GGCCGNNNCC GGGCTCCACC GCCCCCNNNG CCCACGGTGT CACCTCGGCC   2640

CCGGACNNNA GGCCGNNNCC GGGCTCCACC GCCCCCNNNG CCCACGGTGT CACCTCGGCC   2700
```

```
CCGGACNNNA GGCCGNNNCC GGGCTCCACC GCCCCCNNNG CCCACGGTGT CACCTCGGCC    2760

CCGGACNNNA GGCCGNNNCC GGGCTCCACC GCCCCCNNNG CCCACGGTGT CACCTCGGCC    2820

CCGGACNNNA GGCCGNNNCC GGGCTCCACC GCCCCCNNNG CCCACGGTGT CACCTCGGCC    2880

CCGGACNNNA GGCCGNNNCC GGGCTCCACC GCCCCCNNNG CCCACGGTGT CACCTCGGCC    2940

CCGGACNNNA GGCCGNNNCC GGGCTCCACC GCCCCCNNNG CCCACGGTGT CACCTCGGCC    3000

CCGGACNNNA GGCCGNNNCC GGGCTCCACC GCCCCCNNNG CCCACGGTGT CACCTCGGCC    3060

CCGGACNNNA GGCCGNNNCC GGGCTCCACC GCCCCCNNNG CCCACGGTGT CACCTCGGCC    3120

CCGGACNNNA GGCCGNNNCC GGGCTCCACC GCCCCCNNNG CCCACGGTGT CACCTCGGCC    3180

CCGGACNNNA GGCCGNNNCC GGGCTCCACC GCCCCCNNNG CCCACGGTGT CACCTCGGCC    3240

CCGGACNNNA GGCCGNNNCC GGGCTCCACC GCCCCCNNNG CCCACGGTGT CACCTCGGCC    3300

CCGGACNNNA GGCCGNNNCC GGGCTCCACC GCCCCCNNNG CCCACGGTGT CACCTCGGCC    3360

CCGGACNNNA GGCCGNNNCC GGGCTCCACC GCCCCCNNNG CCCACGGTGT CACCTCGGCC    3420

CCGGACNNNA GGCCGNNNCC GGGCTCCACC GCCCCCNNNG CCCACGGTGT CACCTCGGCC    3480

CCGGACNNNA GGCCGNNNCC GGGCTCCACC GCCCCCNNNG CCCACGGTGT CACCTCGGCC    3540

CCGGACNNNA GGCCGNNNCC GGGCTCCACC GCCCCCNNNG CCCACGGTGT CACCTCGGCC    3600

CCGGACNNNA GGCCGNNNCC GGGCTCCACC GCCCCCNNNG CCCACGGTGT CACCTCGGCC    3660

CCGGACNNNA GGCCGNNNCC GGGCTCCACC GCCCCCNNNG CCCACGGTGT CACCTCGGCC    3720

CCGGACNNNA GGCCGNNNCC GGGCTCCACC GCCCCCNNNG CCCACGGTGT CACCTCGGCC    3780

CCGGACNNNA GGCCGNNNCC GGGCTCCACC GCCCCCNNNG CCCACGGTGT CACCTCGGCC    3840

CCGGACNNNA GGCCGNNNCC GGGCTCCACC GCCCCCNNNG CCCACGGTGT CACCTCGGCC    3900

CCGGACNNNA GGCCGNNNCC GGGCTCCACC GCCCCCNNNG CCCACGGTGT CACCTCGGCC    3960

CCGGACNNNA GGCCGNNNCC GGGCTCCACC GCCCCCNNNG CCCACGGTGT CACCTCGGCC    4020

CCGGACNNNA GGCCGNNNCC GGGCTCCACC GCCCCCNNNG CCCACGGTGT CACCTCGGCC    4080

CCGGACNNNA GGCCGNNNCC GGGCTCCACC GCCCCCNNNG CCCACGGTGT CACCTCGGCC    4140

CCGGACNNNA GGCCGNNNCC GGGCTCCACC GCCCCCNNNG CCCACGGTGT CACCTCGGCC    4200

CCGGACNNNA GGCCGNNNCC GGGCTCCACC GCCCCCNNNG CCCACGGTGT CACCTCGGCC    4260

CCGGACNNNA GGCCGNNNCC GGGCTCCACC GCCCCCNNNG CCCACGGTGT CACCTCGGCC    4320

CCGGACNNNA GGCCGNNNCC GGGCTCCACC GCCCCCNNNG CCCACGGTGT CACCTCGGCC    4380

CCGGACNNNA GGCCGNNNCC GGGCTCCACC GCCCCCNNNG CCCACGGTGT CACCTCGGCC    4440

CCGGACNNNA GGCCGNNNCC GGGCTCCACC GCCCCCNNNG CCCACGGTGT CACCTCGGCC    4500

CCGGACNNNA GGCCGNNNCC GGGCTCCACC GCCCCCNNNG CCCACGGTGT CACCTCGGCC    4560

CCGGACNNNA GGCCGNNNCC GGGCTCCACC GCCCCCNNNG CCCACGGTGT CACCTCGGCC    4620

CCGGACNNNA GGCCGNNNCC GGGCTCCACC GCCCCCNNNG CCCACGGTGT CACCTCGGCC    4680

CCGGACNNNA GGCCGNNNCC GGGCTCCACC GCCCCCNNNG CCCACGGTGT CACCTCGGCC    4740

CCGGACNNNA GGCCGNNNCC GGGCTCCACC GCCCCCNNNG CCCACGGTGT CACCTCGGCC    4800

CCGGACNNNA GGCCGNNNCC GGGCTCCACC GCCCCCNNNG CCCACGGTGT CACCTCGGCC    4860

CCGGACNNNA GGCCGNNNCC GGGCTCCACC GCCCCCNNNG CCCACGGTGT CACCTCGGCC    4920

CCGGACNNNA GGCCGNNNCC GGGCTCCACC GCCCCCNNNG CCCACGGTGT CACCTCGGCC    4980

CCGGACNNNA GGCCGNNNCC GGGCTCCACC GCCCCCNNNG CCCACGGTGT CACCTCGGCC    5040
```

-continued

```
CCGGACNNNA GGCCGNNNCC GGGCTCCACC GCCCCCNNNG CCCACGGTGT CACCTCGGCC      5100

CCGGACNNNA GGCCGNNNCC GGGCTCCACC GCCCCCNNNG CCCACGGTGT CACCTCGGCC      5160

CCGGACNNNA GGCCGNNNCC GGGCTCCACC GCCCCCNNNG CCCACGGTGT CACCTCGGCC      5220

CCGGACNNNA GGCCGNNNTT GGGCTCCACC GCCCCTCCAG TCCACAATGT CACCTCGGCC      5280

TCAGGCTCTG CATCAGGCTC AGCTTCTACT CTGGTGCACA ACGGCACCTC TGCCAGGGCT      5340

ACCACAACCC CAGCCAGCAA GAGCACTCCA TTCTCAATTC CCAGCCACCA CTCTGATACT      5400

CCTACCACCC TTGCCAGCCA TAGCACCAAG ACTGATGCCA GTAGCACTCA CCATAGCACG      5460

GTACCTCCTC TCACCTCCTC CAATCACAGC ACTTCTCCCC AGTTGTCTAC TGGGGTCTCT      5520

TTCTTTTTCC TGTCTTTTCA CATTTCAAAC CTCCAGTTTA ATTCCTCTCT GGAAGATCCC      5580

AGCACCGACT ACTACCAAGA GCTGCAGAGA GACATTTCTG AAATGGTGAG TATCGGCCTT      5640

TCCTTCCCCA TGCTCCCCTG AAGCAGCCAT CAGAACTGTC CACACCCTTT GCATCAAGCC      5700

TGAGTCCTTT CCCTCTCACC CCAGTTTTTG CAGATTTATA ACAAGGGGG TTTTCTGGGC       5760

CTCTCCAATA TTAAGTTCAG GTACAGTTCT GGGTGTGGAC CCAGTGTGGT GGTTGGAGGG     5820

TTGGGTGGTG GTCATGACCG TAGGAGGGAC TGGTCGCACT TAAGGTTGGG GGAAGAGTCG     5880

TGAGCCAGAG CTGGGACCCG TGGCTGAAGT GCCCATTTCC CTGTGACCAG GCCAGGATCT     5940

GTGGTGGTAC AATTGACTCT GGCCTTCCGA GAAGGTACCA TCAATGTCCA CGACGTGGAG     6000

ACACAGTTCA ATCAGTATAA AACGGAAGCA GCCTCTCGAT ATAACCTGAC GATCTCAGAC     6060

GTCAGCGGTG AGGCTACTTC CCTGGCTGCA GCCCAGCACC ATGCCGGGGC CCTCTCCTTC     6120

CAGTGCCTGG GTCCCCGCTC TTTCCTTAGT GCTGGCAGCG GGAGGGGCGC CTCCTCTGGG     6180

AGACTGCCCT GACCACTGCT TTTCCTTTTA GTGAGTCATG TGCCATTTCC TTTCTCTGCC     6240

CAGTCTGGGG CTGGGGTGCC AGGCTGGGGC ATCGCGCTGC TGGTGCTGGT CTGTGTTCTG     6300

GTTGCGCTGG CCATTGTCTA TCTCATTGCC TTGGTGAGTG CAGTCCCTGG CCCTGATCAG     6360

AGCCCCCCGT TAGAAGGCAC TCCATGGCCT GCCATAACCT CCTATCTCCC CAGGCTGTCT     6420

GTCAGTGCCG CCGAAAGAAC TACGGGCAG                                        6449
```

(2) INFORMATION FOR SEQ ID NO:5:

(i) SEQUENCE CHARACTERISTICS:
        (A) LENGTH: 1867 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 128..1727
        (D) OTHER INFORMATION: /note= "The amino acids spanning
            128 to 1727 constitute a repeated region wherein the
            repeat is 20 amino acids, 17 of which are fixed. The
            number of such repeats varies from 1 to 40."

(ix) FEATURE:
        (A) NAME/KEY: Peptide
        (B) LOCATION: 134
        (D) OTHER INFORMATION: /note= "Amino acid 134 is X1 = Xaa
            which is the codon for Pro or Ala wherein Pro = CCT, CCC,
            CCA, or CCG; and Ala = GCT, GCC, GCA, or GCG."

(ix) FEATURE:
        (A) NAME/KEY: Peptide
        (B) LOCATION: 144
        (D) OTHER INFORMATION: /note= "Amino acid 144 is Y = Xaa
            which is the codon for Thr or Asn wherein Thr = ACT, ACC, ACA, or ACG; and Asn = AAT or AAC."

(ix) FEATURE:
    (A) NAME/KEY: Peptide
    (B) LOCATION: 147
    (D) OTHER INFORMATION: /note= "Amino acid 147 is X2 = Xaa
        which is the codon for Pro or Ala wherein Pro = CCT, CCC,
        CCA, or CCG; and Ala = GCT, GCC, GCA, or GCG."

(ix) FEATURE:
    (A) NAME/KEY: Peptide
    (B) LOCATION: 1..21
    (D) OTHER INFORMATION: /note= "Amino acids 1 to 21 are a
        21 amino acid precursor sequence."

(xi) SEQUENCE DESCRIPTION: SEQ ID NO:5:

```
Met Thr Pro Gly Thr Gln Ser Pro Phe Phe Leu Leu Leu Leu Thr
 1               5                  10                  15

Val Leu Thr Val Val Thr Gly Ser Gly His Ala Ser Ser Thr Pro Gly
                20                  25                  30

Gly Glu Lys Glu Thr Ser Ala Thr Gln Arg Ser Ser Val Pro Ser Ser
                35                  40                  45

Thr Glu Lys Asn Ala Val Ser Met Thr Ser Ser Val Leu Ser Ser His
 50                  55                  60

Ser Pro Gly Ser Gly Ser Ser Thr Thr Gln Gly Gln Asp Val Thr Leu
65                  70                  75                  80

Ala Pro Ala Thr Glu Pro Ala Ser Gly Ser Ala Ala Thr Trp Gly Gln
                85                  90                  95

Asp Val Thr Ser Val Pro Val Thr Arg Pro Ala Leu Gly Ser Thr Thr
                100                 105                 110

Pro Pro Ala His Asp Val Thr Ser Ala Pro Asp Asn Lys Pro Ala Pro
                115                 120                 125

Gly Ser Thr Ala Pro Xaa Ala His Gly Val Thr Ser Ala Pro Asp Xaa
    130                 135                 140

Arg Pro Xaa Pro Gly Ser Thr Ala Pro Xaa Ala His Gly Val Thr Ser
145                 150                 155                 160

Ala Pro Asp Xaa Arg Pro Xaa Pro Gly Ser Thr Ala Pro Xaa Ala His
                165                 170                 175

Gly Val Thr Ser Ala Pro Asp Xaa Arg Pro Xaa Pro Gly Ser Thr Ala
                180                 185                 190

Pro Xaa Ala His Gly Val Thr Ser Ala Pro Asp Xaa Arg Pro Xaa Pro
    195                 200                 205

Gly Ser Thr Ala Pro Xaa Ala His Gly Val Thr Ser Ala Pro Asp Xaa
    210                 215                 220

Arg Pro Xaa Pro Gly Ser Thr Ala Pro Xaa Ala His Gly Val Thr Ser
225                 230                 235                 240

Ala Pro Asp Xaa Arg Pro Xaa Pro Gly Ser Thr Ala Pro Xaa Ala His
                245                 250                 255

Gly Val Thr Ser Ala Pro Asp Xaa Arg Pro Xaa Pro Gly Ser Thr Ala
                260                 265                 270

Pro Xaa Ala His Gly Val Thr Ser Ala Pro Asp Xaa Arg Pro Xaa Pro
    275                 280                 285

Gly Ser Thr Ala Pro Xaa Ala His Gly Val Thr Ser Ala Pro Asp Xaa
    290                 295                 300

Arg Pro Xaa Pro Gly Ser Thr Ala Pro Xaa Ala His Gly Val Thr Ser
305                 310                 315                 320

Ala Pro Asp Xaa Arg Pro Xaa Pro Gly Ser Thr Ala Pro Xaa Ala His
                325                 330                 335
```

-continued

```
Gly Val Thr Ser Ala Pro Asp Xaa Arg Pro Xaa Pro Gly Ser Thr Ala
            340                 345                 350
Pro Xaa Ala His Gly Val Thr Ser Ala Pro Asp Xaa Arg Pro Xaa Pro
        355                 360                 365
Gly Ser Thr Ala Pro Xaa Ala His Gly Val Thr Ser Ala Pro Asp Xaa
    370                 375                 380
Arg Pro Xaa Pro Gly Ser Thr Ala Pro Xaa Ala His Gly Val Thr Ser
385                 390                 395                 400
Ala Pro Asp Xaa Arg Pro Xaa Pro Gly Ser Thr Ala Pro Xaa Ala His
                405                 410                 415
Gly Val Thr Ser Ala Pro Asp Xaa Arg Pro Xaa Pro Gly Ser Thr Ala
            420                 425                 430
Pro Xaa Ala His Gly Val Thr Ser Ala Pro Asp Xaa Arg Pro Xaa Pro
        435                 440                 445
Gly Ser Thr Ala Pro Xaa Ala His Gly Val Thr Ser Ala Pro Asp Xaa
    450                 455                 460
Arg Pro Xaa Pro Gly Ser Thr Ala Pro Xaa Ala His Gly Val Thr Ser
465                 470                 475                 480
Ala Pro Asp Xaa Arg Pro Xaa Pro Gly Ser Thr Ala Pro Xaa Ala His
                485                 490                 495
Gly Val Thr Ser Ala Pro Asp Xaa Arg Pro Xaa Pro Gly Ser Thr Ala
            500                 505                 510
Pro Xaa Ala His Gly Val Thr Ser Ala Pro Asp Xaa Arg Pro Xaa Pro
        515                 520                 525
Gly Ser Thr Ala Pro Xaa Ala His Gly Val Thr Ser Ala Pro Asp Xaa
    530                 535                 540
Arg Pro Xaa Pro Gly Ser Thr Ala Pro Xaa Ala His Gly Val Thr Ser
545                 550                 555                 560
Ala Pro Asp Xaa Arg Pro Xaa Pro Gly Ser Thr Ala Pro Xaa Ala His
                565                 570                 575
Gly Val Thr Ser Ala Pro Asp Xaa Arg Pro Xaa Pro Gly Ser Thr Ala
            580                 585                 590
Pro Xaa Ala His Gly Val Thr Ser Ala Pro Asp Xaa Arg Pro Xaa Pro
        595                 600                 605
Gly Ser Thr Ala Pro Xaa Ala His Gly Val Thr Ser Ala Pro Asp Xaa
    610                 615                 620
Arg Pro Xaa Pro Gly Ser Thr Ala Pro Xaa Ala His Gly Val Thr Ser
625                 630                 635                 640
Ala Pro Asp Xaa Arg Pro Xaa Pro Gly Ser Thr Ala Pro Xaa Ala His
                645                 650                 655
Gly Val Thr Ser Ala Pro Asp Xaa Arg Pro Xaa Pro Gly Ser Thr Ala
            660                 665                 670
Pro Xaa Ala His Gly Val Thr Ser Ala Pro Asp Xaa Arg Pro Xaa Pro
        675                 680                 685
Gly Ser Thr Ala Pro Xaa Ala His Gly Val Thr Ser Ala Pro Asp Xaa
    690                 695                 700
Arg Pro Xaa Pro Gly Ser Thr Ala Pro Xaa Ala His Gly Val Thr Ser
705                 710                 715                 720
Ala Pro Asp Xaa Arg Pro Xaa Pro Gly Ser Thr Ala Pro Xaa Ala His
                725                 730                 735
Gly Val Thr Ser Ala Pro Asp Xaa Arg Pro Xaa Pro Gly Ser Thr Ala
            740                 745                 750
```

```
Pro Xaa Ala His Gly Val Thr Ser Ala Pro Asp Xaa Arg Pro Xaa Pro
        755                 760                 765

Gly Ser Thr Ala Pro Xaa Ala His Gly Val Thr Ser Ala Pro Asp Xaa
    770                 775                 780

Arg Pro Xaa Pro Gly Ser Thr Ala Pro Xaa Ala His Gly Val Thr Ser
785                 790                 795                 800

Ala Pro Asp Xaa Arg Pro Xaa Pro Gly Ser Thr Ala Pro Xaa Ala His
            805                 810                 815

Gly Val Thr Ser Ala Pro Asp Xaa Arg Pro Xaa Pro Gly Ser Thr Ala
            820                 825                 830

Pro Xaa Ala His Gly Val Thr Ser Ala Pro Asp Xaa Arg Pro Xaa Pro
        835                 840                 845

Gly Ser Thr Ala Pro Xaa Ala His Gly Val Thr Ser Ala Pro Asp Xaa
    850                 855                 860

Arg Pro Xaa Pro Gly Ser Thr Ala Pro Xaa Ala His Gly Val Thr Ser
865                 870                 875                 880

Ala Pro Asp Xaa Arg Pro Xaa Pro Gly Ser Thr Ala Pro Xaa Ala His
            885                 890                 895

Gly Val Thr Ser Ala Pro Asp Xaa Arg Pro Xaa Pro Gly Ser Thr Ala
            900                 905                 910

Pro Xaa Ala His Gly Val Thr Ser Ala Pro Asp Xaa Arg Pro Xaa Pro
        915                 920                 925

Gly Ser Thr Ala Pro Xaa Ala His Gly Val Thr Ser Ala Pro Asp Xaa
    930                 935                 940

Arg Pro Xaa Pro Gly Ser Thr Ala Pro Xaa Ala His Gly Val Thr Ser
945                 950                 955                 960

Ala Pro Asp Xaa Arg Pro Xaa Pro Gly Ser Thr Ala Pro Xaa Ala His
            965                 970                 975

Gly Val Thr Ser Ala Pro Asp Xaa Arg Pro Xaa Pro Gly Ser Thr Ala
            980                 985                 990

Pro Xaa Ala His Gly Val Thr Ser Ala Pro Asp Xaa Arg Pro Xaa Pro
        995                 1000                1005

Gly Ser Thr Ala Pro Xaa Ala His Gly Val Thr Ser Ala Pro Asp Xaa
    1010                1015                1020

Arg Pro Xaa Pro Gly Ser Thr Ala Pro Xaa Ala His Gly Val Thr Ser
1025                1030                1035                1040

Ala Pro Asp Xaa Arg Pro Xaa Pro Gly Ser Thr Ala Pro Xaa Ala His
            1045                1050                1055

Gly Val Thr Ser Ala Pro Asp Xaa Arg Pro Xaa Pro Gly Ser Thr Ala
            1060                1065                1070

Pro Xaa Ala His Gly Val Thr Ser Ala Pro Asp Xaa Arg Pro Xaa Pro
        1075                1080                1085

Gly Ser Thr Ala Pro Xaa Ala His Gly Val Thr Ser Ala Pro Asp Xaa
    1090                1095                1100

Arg Pro Xaa Pro Gly Ser Thr Ala Pro Xaa Ala His Gly Val Thr Ser
1105                1110                1115                1120

Ala Pro Asp Xaa Arg Pro Xaa Pro Gly Ser Thr Ala Pro Xaa Ala His
            1125                1130                1135

Gly Val Thr Ser Ala Pro Asp Xaa Arg Pro Xaa Pro Gly Ser Thr Ala
            1140                1145                1150

Pro Xaa Ala His Gly Val Thr Ser Ala Pro Asp Xaa Arg Pro Xaa Pro
        1155                1160                1165

Gly Ser Thr Ala Pro Xaa Ala His Gly Val Thr Ser Ala Pro Asp Xaa
```

-continued

```
            1170                1175                1180
Arg Pro Xaa Pro Gly Ser Thr Ala Pro Xaa Ala His Gly Val Thr Ser
1185                1190                1195                1200
Ala Pro Asp Xaa Arg Pro Xaa Pro Gly Ser Thr Ala Pro Xaa Ala His
                1205                1210                1215
Gly Val Thr Ser Ala Pro Asp Xaa Arg Pro Xaa Pro Gly Ser Thr Ala
            1220                1225                1230
Pro Xaa Ala His Gly Val Thr Ser Ala Pro Asp Xaa Arg Pro Xaa Pro
        1235                1240                1245
Gly Ser Thr Ala Pro Xaa Ala His Gly Val Thr Ser Ala Pro Asp Xaa
    1250                1255                1260
Arg Pro Xaa Pro Gly Ser Thr Ala Pro Xaa Ala His Gly Val Thr Ser
1265                1270                1275                1280
Ala Pro Asp Xaa Arg Pro Xaa Pro Gly Ser Thr Ala Pro Xaa Ala His
                1285                1290                1295
Gly Val Thr Ser Ala Pro Asp Xaa Arg Pro Xaa Pro Gly Ser Thr Ala
            1300                1305                1310
Pro Xaa Ala His Gly Val Thr Ser Ala Pro Asp Xaa Arg Pro Xaa Pro
        1315                1320                1325
Gly Ser Thr Ala Pro Xaa Ala His Gly Val Thr Ser Ala Pro Asp Xaa
    1330                1335                1340
Arg Pro Xaa Pro Gly Ser Thr Ala Pro Xaa Ala His Gly Val Thr Ser
1345                1350                1355                1360
Ala Pro Asp Xaa Arg Pro Xaa Pro Gly Ser Thr Ala Pro Xaa Ala His
                1365                1370                1375
Gly Val Thr Ser Ala Pro Asp Xaa Arg Pro Xaa Pro Gly Ser Thr Ala
            1380                1385                1390
Pro Xaa Ala His Gly Val Thr Ser Ala Pro Asp Xaa Arg Pro Xaa Pro
        1395                1400                1405
Gly Ser Thr Ala Pro Xaa Ala His Gly Val Thr Ser Ala Pro Asp Xaa
    1410                1415                1420
Arg Pro Xaa Pro Gly Ser Thr Ala Pro Xaa Ala His Gly Val Thr Ser
1425                1430                1435                1440
Ala Pro Asp Xaa Arg Pro Xaa Pro Gly Ser Thr Ala Pro Xaa Ala His
                1445                1450                1455
Gly Val Thr Ser Ala Pro Asp Xaa Arg Pro Xaa Pro Gly Ser Thr Ala
            1460                1465                1470
Pro Xaa Ala His Gly Val Thr Ser Ala Pro Asp Xaa Arg Pro Xaa Pro
        1475                1480                1485
Gly Ser Thr Ala Pro Xaa Ala His Gly Val Thr Ser Ala Pro Asp Xaa
    1490                1495                1500
Arg Pro Xaa Pro Gly Ser Thr Ala Pro Xaa Ala His Gly Val Thr Ser
1505                1510                1515                1520
Ala Pro Asp Xaa Arg Pro Xaa Pro Gly Ser Thr Ala Pro Xaa Ala His
                1525                1530                1535
Gly Val Thr Ser Ala Pro Asp Xaa Arg Pro Xaa Pro Gly Ser Thr Ala
            1540                1545                1550
Pro Xaa Ala His Gly Val Thr Ser Ala Pro Asp Xaa Arg Pro Xaa Pro
        1555                1560                1565
Gly Ser Thr Ala Pro Xaa Ala His Gly Val Thr Ser Ala Pro Asp Xaa
    1570                1575                1580
Arg Pro Xaa Pro Gly Ser Thr Ala Pro Xaa Ala His Gly Val Thr Ser
1585                1590                1595                1600
```

-continued

```
Ala Pro Asp Xaa Arg Pro Xaa Pro Gly Ser Thr Ala Pro Xaa Ala His
            1605            1610                1615

Gly Val Thr Ser Ala Pro Asp Xaa Arg Pro Xaa Pro Gly Ser Thr Ala
            1620            1625            1630

Pro Xaa Ala His Gly Val Thr Ser Ala Pro Asp Xaa Arg Pro Xaa Pro
        1635            1640            1645

Gly Ser Thr Ala Pro Xaa Ala His Gly Val Thr Ser Ala Pro Asp Xaa
        1650            1655            1660

Arg Pro Xaa Pro Gly Ser Thr Ala Pro Xaa Ala His Gly Val Thr Ser
1665            1670            1675            1680

Ala Pro Asp Xaa Arg Pro Xaa Pro Gly Ser Thr Ala Pro Xaa Ala His
            1685            1690                1695

Gly Val Thr Ser Ala Pro Asp Xaa Arg Pro Xaa Pro Gly Ser Thr Ala
            1700            1705            1710

Pro Xaa Ala His Gly Val Thr Ser Ala Pro Asp Xaa Arg Pro Xaa Leu
        1715            1720            1725

Gly Ser Thr Ala Pro Pro Val His Asn Val Thr Ser Ala Ser Gly Ser
        1730            1735            1740

Ala Ser Gly Ser Ala Ser Thr Leu Val His Asn Gly Thr Ser Ala Arg
1745            1750            1755            1760

Ala Thr Thr Thr Pro Ala Ser Lys Ser Thr Pro Phe Ser Ile Pro Ser
            1765            1770            1775

His His Ser Asp Thr Pro Thr Thr Leu Ala Ser His Ser Thr Lys Thr
            1780            1785            1790

Asp Ala Ser Ser Thr His His Ser Thr Val Pro Pro Leu Thr Ser Ser
            1795            1800            1805

Asn His Ser Thr Ser Pro Gln Leu Ser Thr Gly Val Ser Phe Phe Phe
    1810            1815            1820

Leu Ser Phe His Ile Ser Asn Leu Gln Phe Asn Ser Ser Leu Glu Asp
1825            1830            1835            1840

Pro Ser Thr Asp Tyr Tyr Gln Glu Leu Gln Arg Asp Ile Ser Glu Met
            1845            1850            1855

Val Ser Ile Gly Leu Ser Phe Pro Met Leu Pro
            1860            1865
```

What is claimed is:

1. A pharmaceutical composition which comprises, as therapeutic agent, a polypeptide recognized by antibody H23, said polypeptide comprising a sequence repeated n times, n being a number from 1 to 80; and of formula (I): Pro—Gly—Ser—Thr—Ala—Pro—$X_1$—Ala—His—Gly—Val—Thr—Ser—Ala—Pro—Asp—Y—Arg—Pro—$X_2$ (SEQ ID NO: 3) in which $X_1$, and $X_2$ are, independently, Pro or Ala and Y is Thr or Asn; and said polypeptide comprising a sequence selected from the group consisting of (i) the sequence as shown in SEQ ID NO: 2 beginning with the threonine residue at position 22 and ending with the leucine residue at position 2035 or a sequence identical thereto except that the number of repeated sequences having SEQ ID NO: 3 ranges from 1 to 79, (ii) the sequence as shown in SEQ ID NO: 5 beginning with the threonine residue at position 22 and ending with the proline residue at position 1867, or a sequence identical thereto, except that the number of repeated sequences having SEQ ID NO: 3 ranges from 1 to 79, (iii) variants of the sequences set forth in (i) or (ii), wherein such variants differ from the sequence set forth in (i) or (ii), only in the fact that one or more of the repeat sequences contained therein differs from the repeat sequence of SEQ ID NO: 3 at no more than three amino acid positions, and (iv) fragments of any of said sequences set forth in (i), (ii) or (iii), wherein said fragment is a polypeptide that is recognized by antibody H23, and a pharmaceutically acceptable diluent or vehicle.

2. A composition according to claim 1, which comprises a polypeptide recognized by antibody H23, said polypeptide having as its sequence (i) the sequence as shown in SEQ ID NO: 2 beginning with the threonine residue at position 22 and ending with the leucine residue at position 2035, except that the number of repeated sequences having SEQ ID NO: 3 ranges from 2 to 4, or (ii) the sequence as shown in SEQ ID No. 5, beginning with the threonine residue at position 22 and ending with the proline residue at position 1867, except that the number of repeated sequences having SEQ ID NO: 3 ranges from 2 to 4, and a pharmaceutically acceptable diluent or vehicle.

3. The pharmaceutical composition of claim 1, wherein $X_1$ is Pro.

4. The pharmaceutical composition of claim 1, wherein $X_1$ is Ala.

5. The pharmaceutical composition of claim 1, wherein X₂ is Pro.

6. The pharmaceutical composition of claim 1, wherein X₂ is Ala.

7. The pharmaceutical composition of claim 1, wherein Y is Thr.

8. The pharmaceutical composition of claim 1, wherein Y is Asn.

9. The pharmaceutical composition of claim 1, wherein the polypeptide has the sequence shown in SEQ ID NO: 5, and the number of repeats n of SEQ ID NO: 3 is 2, 3 or 4.

10. The pharmaceutical composition according to claim 1, wherein the number of repeated sequences in the polypeptide ranges from 1 to 40.

11. The pharmaceutical composition of claim 1, wherein the polypeptide has the sequence shown in SEQ ID NO: 2, and the number of repeats n of SEQ ID NO: 3 is 2,3 or 4.

12. A method of treating or preventing a malignancy characterized by malignant tumors that express elevated amounts of the antigen recognized by the H23 antibody comprising administering a therapeutically or prophylactically effective amount of the pharmaceutical composition of claim 1.

13. The pharmaceutical composition of claim 9, wherein n is 4.

14. The pharmaceutical composition of claim 11, wherein n is 4.

15. The method of claim 12, wherein said malignancy is a breast cancer.

16. The method of claim 12, wherein said malignancy is characterized by tumoral epithelial tissues that express elevated amounts of the antigen recognized by the H23 antibody.

17. A polypeptide which comprises a sequence repeated n times, n being a number from 1 to 4; and of formula (I): Pro—Gly—Ser—Thr—Ala—Pro—X₁—Ala—His—Gly—Val—Thr—Ser—Ala—Pro—Asp—Y—Arg—Pro—X₂ (SEQ ID NO: 3) in which X₁ and X₂ are, independently, Pro or Ala and Y is Thr or Asn; and said polypeptide comprising a sequence selected from the group consisting of (i) the sequence as shown in SEQ ID NO: 2 beginning with the threonine residue at position 22 and ending with the leucine residue at position 2035 or a sequence identical thereto except that the number of repeated sequences having SEQ ID NO: 3 ranges from 1 to [4, (ii) the sequence as shown in SEQ ID NO: 5 beginning with the threonine residue at position 22 and ending with the proline residue at position 1867, or a sequence identical thereto, except that the number of repeated sequences having SEQ ID NO: 3 ranges from 1 to 4, (iii) variants of the sequences set forth in (i) or (ii), wherein such variants differ from the sequence set forth in (i) or (ii), only in the fact that one or more of the repeat sequences contained therein differs from the repeat sequence of SEQ ID NO: 3 at no more than three amino acid positions, and (iv) fragments of any of said sequences set forth in (i), (ii) or (iii), wherein said fragment is a polypeptide that is recognized by antibody H23.

18. An isolated polypeptide according to claim 17, having as its sequence (i) the sequence as shown in SEQ ID NO: 2 beginning with the threonine residue at position 22 and ending with the leucine residue at position 2035, except that the number of repeated sequences having SEQ ID NO: 3 ranges from 2 to 4, or (ii) the sequence as shown in SEQ ID NO: 5, beginning with the threonine residue at position 22 and ending with the proline residue at position 1867, except that the number of repeated sequences having SEQ ID NO: 3 ranges from 2 to 4.

19. The polypeptide of claim 17, wherein X₁ is Pro.

20. The polypeptide of claim 17, wherein X₁ is Ala.

21. The polypeptide of claim 17, wherein X₂ is Pro.

22. The polypeptide of claim 17, wherein X₂ is Ala.

23. The polypeptide of claim 17, wherein Y is Thr.

24. The polypeptide of claim 17, wherein Y is Asn.

25. The polypeptide of claim 17, wherein the polypeptide has the sequence shown in SEQ ID NO: 5, and the number of repeats n of SEQ ID NO: 3 is 2, 3 or 4.

26. The polypeptide of claim 17, wherein the polypeptide has the sequence shown in SEQ ID NO: 2, and the number of repeats n of SEQ ID NO: 3 is 2, 3 or 4.

27. The polypeptide of claim 17, wherein n is 4.

28. The polypeptide of claim 26, wherein n is 4.

29. A composition which comprises a polypeptide recognized by antibody H23, said polypeptide comprising a sequence repeated n times, n being a number from 1 to 4; and of formula (I): Pro—Gly—Ser—Thr—Ala—Pro—X₁—Ala—His—Gly—Val—Thr—Ser—Ala—Pro—Asp—Y—Arg—Pro—X₂ SEQ ID NO:3 in which X₁ and X₂ are, independently, Pro or Ala and Y is Thr or Asn; and said polypeptide comprising a sequence selected from the group consisting of (i) the sequence as shown in SEQ ID NO:2 beginning with the threonine residue at position 22 and ending with the leucine residue at position 2035 or a sequence identical thereto except that the number of repeated sequences having SEQ ID NO:3 ranges from 1 to 4, (ii) the sequence as shown in SEQ ID NO:5 beginning with the threonine residue at position 22 and ending with the proline residue at position 1867, or a sequence identical thereto, except that the number of repeated sequences having SEQ ID NO:3 ranges from 1 to 4, (iii) variants of the sequences set forth in (i) or (ii), wherein such variants differ from the sequence set forth in (i) or (ii), only in the fact that one or more of the repeat sequences contained therein differs from the repeat sequence of SEQ ID NO:3 at no more than three amino acid positions, and (iv) fragments of any of said sequences set forth in (i), (ii) or (iii), wherein said fragment is a polypeptide that is recognized by antibody H23.

30. A composition according to claim 29, which comprises a polypeptide recognized by antibody H23, said polypeptide having as its sequence (i) the sequence as shown in SEQ ID NO:2 beginning with the threonine residue at position 22 and ending with the leucine residue at position 2035, except that the number of repeated sequences having SEQ ID NO:3 ranges from 2 to 4, or (ii) the sequence as shown in SEQ ID NO:5, beginning with the threonine residue at position 22 and ending with the proline residue at position 1867, except that the number of repeated sequences having SEQ ID NO:3 ranges from 2 to 4, and a pharmaceutically acceptable diluent or vehicle.

31. The composition of claim 29, wherein X₁ is Pro.

32. The composition of claim 29, wherein X₁ is Ala.

33. The composition of claim 29, wherein X₂ is Pro.

34. The composition of claim 29, wherein X₂ is Ala.

35. The composition of claim 29, wherein Y is Thr.

36. The composition of claim 29, wherein Y is Asn.

37. The composition of claim 29, wherein the polypeptide has the sequence shown in SEQ ID NO:5, and the number of repeats n of SEQ ID NO:3 is 2, 3 or 4.

38. The composition of claim 29, wherein the polypeptide has the sequence shown in SEQ ID NO:2, and the number of repeats n of SEQ ID NO:3 is 2, 3 or 4.

39. The composition of claim 37, wherein n is 4.

40. The composition of claim 38, wherein n is 4.

* * * * *